(12) United States Patent
Yaffe et al.

(10) Patent No.: US 12,115,171 B2
(45) Date of Patent: *Oct. 15, 2024

(54) COMBINATION THERAPIES AND METHODS OF USE THEREOF FOR TREATING CANCER

(71) Applicant: Massachusetts Institute of Technology, Cambridge, MA (US)

(72) Inventors: Michael B. Yaffe, West Roxbury, MA (US); Jesse C. Patterson, Natick, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/836,836

(22) Filed: Jun. 9, 2022

(65) Prior Publication Data

US 2023/0103366 A1 Apr. 6, 2023

Related U.S. Application Data

(63) Continuation of application No. 16/996,625, filed on Aug. 18, 2020, now abandoned, which is a continuation of application No. 16/222,459, filed on Dec. 17, 2018, now Pat. No. 10,772,898, which is a continuation of application No. 15/431,312, filed on Feb. 13, 2017, now Pat. No. 10,155,006, which is a continuation of application No. 14/607,732, filed on Jan. 28, 2015, now Pat. No. 9,566,280.

(60) Provisional application No. 61/932,283, filed on Jan. 28, 2014.

(51) Int. Cl.
| | |
|---|---|
| A61K 31/58 | (2006.01) |
| A61K 31/337 | (2006.01) |
| A61K 31/4409 | (2006.01) |
| A61K 31/4439 | (2006.01) |
| A61K 31/496 | (2006.01) |
| A61K 31/519 | (2006.01) |
| A61K 31/567 | (2006.01) |
| A61K 31/573 | (2006.01) |
| A61K 31/575 | (2006.01) |
| A61K 45/06 | (2006.01) |

(52) U.S. Cl.
CPC ............ *A61K 31/58* (2013.01); *A61K 31/337* (2013.01); *A61K 31/4409* (2013.01); *A61K 31/4439* (2013.01); *A61K 31/496* (2013.01); *A61K 31/519* (2013.01); *A61K 31/567* (2013.01); *A61K 31/573* (2013.01); *A61K 31/575* (2013.01); *A61K 45/06* (2013.01)

(58) Field of Classification Search
CPC .... A61K 31/58; A61K 31/519; A61K 31/573; A61K 45/06; A61K 31/337; A61K 31/4409; A61K 31/4439; A61K 31/496; A61K 31/596; A61K 31/575
See application file for complete search history.

(56) References Cited

U.S. PATENT DOCUMENTS

| | | | |
|---|---|---|---|
| 5,604,213 | A | 2/1997 | Barrie |
| 6,806,272 | B2 | 10/2004 | Bauer |
| 2001/0051344 | A1 | 12/2001 | Shalon |
| 2010/0004141 | A1 | 1/2010 | Khvorova |
| 2010/0010014 | A1 | 1/2010 | Smith |
| 2010/0048891 | A1 | 2/2010 | Schulze |
| 2010/0093832 | A1 | 4/2010 | Tachas |
| 2012/0295932 | A1 | 11/2012 | Ferlini |
| 2013/0116258 | A1 | 5/2013 | Smith |
| 2013/0122111 | A1 | 5/2013 | Taube |
| 2019/0125732 | A1 | 5/2019 | Sabir |

FOREIGN PATENT DOCUMENTS

| | | |
|---|---|---|
| EP | 2141163 | 1/2010 |
| WO | 200850096 | 5/2008 |
| WO | 2009112524 | 1/2009 |
| WO | 2009128805 | 1/2009 |
| WO | 2010025073 | 1/2010 |
| WO | 2013079964 | 1/2013 |
| WO | 2015116696 | 8/2015 |
| WO | 2019197605 | 10/2019 |

OTHER PUBLICATIONS

Abbou, "Polo-like Kinase Inhibitor Volasertib Exhibits Antitumor Activity and Synergy with Vincristine in Pediatric Malignancies", 599-610 (2016).
Cobb, et al., "Sepsis gene expression profiling: Murine splenic compared with hepatic responses determined by using complemetary DNA microarrays", Crit. Care. Med., 30(12):2711-2721 (2002).
Enard, et al., "Intra- and interspecific variation in primate gene expression patterns", Science, 296(5566):340-343 (2002).
Fan, et al: "Real-time nanoscale proteomic analysis of the novel multi-kinase pathway inhibitor rigosertib to measure the response to treatment of cancer", Expert Opinion on Investigational Drugs, 22(11): 1495-1509 (2013).
Ikezoe, et al: "A novel treatment strategy targeting polo-like kinase 1 in hematological malignancies", Leukemia, 23(9):1564-1576 (2009).
Lucentini, et al., "Gene association Studies Typically Wrong", The Scientist, 18:20 (2004).

(Continued)

*Primary Examiner* — Shirley V Gembeh
(74) *Attorney, Agent, or Firm* — PABST PATENT GROUP LLP

(57) ABSTRACT

Pharmaceutical compositions including an effective amount of an antiandrogen or androgen antagonist in combination with a Plk inhibitor and methods of use thereof for treating cancer are disclosed. Administration of the combination of the active agents can be effective to reduce cancer cell proliferation or viability in a subject with cancer to the same degree, or a greater degree than administering to the subject the same amount of either active agent alone. The active agents can be administered together or separately. Methods of selecting and treating subjects with cancers, particular prostate cancers including castration resistant prostate cancer, breast cancers, particularly androgen receptor positive breast cancers, and pancreatic cancers are also provided.

20 Claims, 16 Drawing Sheets

(56) References Cited

OTHER PUBLICATIONS

Patterson, et al: "VISAGE Reveals a Target able Mitotic Spindle Vulnerability in Cancer Cells", Cell Systems, 9(1):74-92 (2019).
Saatci, et al: "Targeting PLKI overcomes T-DMI resistance via CDKI-dependent phosphorylation and inactivation of Bcl-2/xL in HER2-positive breast cancer", Oncogene, 37(17): 2251-2269 (2018).
Abiraterone plus hormone therapy is an effective treatment for some men with high-risk prostate cancer, Cancer.Net, http://www.cancer.net/cacer-news-and-meetings/asco-annual-meetings/research-summaries., accessed Jan. 22, 2014.
ADIS R&D Profile, "Abiraterone Acetate", Drugs R D, 10(4):261-269 (2010).
Barretina, et al., "The Cancer Cell Line Encyclopedia enables predictive modelling of anticancer drug sensitivity", Nature 483:603-7 (2012).
Beltran, et al., "New therapies for castration-resistant prostate cancer: efficacy and safety", European Urology, 60(2):279-90 (2011).
Brossard, et al., "N-Substituted Piperazinopyridylsteroid Derivatives as Abiraterone Analogues Inhibit Growth and Induce Pro-apoptosis in Human Hormone-independent Prostate Cancer Cell Lines", Chem. Biol. Drug Des., 82:620-629 (2013).
Can Zytiga and provenge be used as combination therapy for prostate cancer?, http://archive.constantcontact.com/s064/1103387863745/archive/110330829627.,Accessed Jan. 22, 2014.
Chen, et al., "Identification of novel, potent and selective inhibitors of Polo-like kinase 1", Bioorg. Med. Chem. Lett., 22(2):1247-50 (2012).
Clegg, et al., "ARN-509: a novel antiandrogen for prostate cancer treatment", Cancer Res., 72:1494-4503 (2012).
Dasmahapatra, et al., "PLK1 inhibitors synergistically potentiate HDAC inhibitor lethality in imatinib mesylate-sensitive or -resistant BCR/ABL+ leukemia cells in vitro and in vivo", Clin Cancer Res., 19(2):404-14 (2013).
De Luca, "Retinoids and their receptors in differentiation, embryogeneisis, and neoplasia", Faseb. J., 5:2924-2933 (1991).
Deeraksa, et al., "Plk1 is upregulated in androgen-insensitive prostate cancer cells and its inhibition leads to necroptosis", Oncogene, 32(24):2973-83 (2013).
Duffey, et al., "Discovery of a potent and orally bioavailable benzolactam-derived inhibitor of Polo-like kinase 1 (MLN0905)", Med Chem, 55(1):197-208 (2012).
Efstathiou, et al., European Cancer Congress, Sep. 27-1, 2013, Amsterdam, TheNetherlands, Abstract 2854).
Ellis, et al., "A phase I open-label dose-escalation study of intravenous BI 2536 together with pemetrexed in previously treated patients with non-small-cell lung cancer", Clin. Lung Cancer, 14(1):19-27 (2013).
Frost, et al., "Phase i study of the Plk1 inhibitor BI 2536 administered intravenously on three consecutive days in advanced solid tumours", Curr. Oncology, 19(1):e28-35 (2012).
Garay, et al., "Androgen receptor as a targeted therapy for breast cancer", Am. J. Cancer Res., 2(4):434-45 (2012).
Garland, et al., "A phase I pharmacokinetic study of HMN-214, a novel oral stilbene derivative with polo-like kinase-1-interacting properties, in patients with advanced solid tumors", Clin. Cancer Res., 1;12(17):5182-9 (2006).
Gianni, et al., "P38MAPK-dependent phosphorylation and degradation of SRC-3/AIB1 and RARalpha-mediated transcription", The EMBO journal, 25:739-51 (2006).
Gianni, et al., "Phosphorylation by p38MAPK and recruitment of SUG-1 are required for RA-induced RAR gamma degradation and transactivation", The EMBO journal, 21:3760-9 (2002).
Gil, et al., "Final analysis of a phase I single dose-escalation study of the novel polo-like kinase 1 inhibitor BI 6727 in patients with advanced solid tumors", J. Clin. Oncol., 28 Suppl 15:abstr 3061 (2010).
Gilmartin, et al., "Distinct concentration-dependent effects of the polo-like kinase 1-specific inhibitor GSK461364A, including differential effect on apoptosis", Cancer Res, 69(17):6969-77 (2009).

Gregg, et al., "Genes and Cancer", Chinese J. of Cancer Research, 2(9):900-909 (2011).
Gumireddy, et al., "ON01910, a non-ATP-competitive small molecule inhibitor of Plk1, is a potent anticancer agent", Cancer Cell, 7:275-86 (2005).
Harris, et al., "Polo-like kinase 1 (PLK1) inhibition suppresses cell growth and enhances radiation sensitivity in medulloblastoma cells", BMC Cancer, 12: 80 (2012).
Hartsink-Segers, et al., "Inhibiting Polo-like kinase 1 causes growth reduction and apoptosis in pediatric acute lymphoblastic leukemia cells", Haematologica., 98(10):1539-46 (2013).
Heidegger, et al., "Novel therapeutic approaches for the treatment of castration-resistant prostate cancer", J. Steroid Biochem. Mol. Biol., 138(100): 248-56 (2013).
Hikichi, et al., "TAK-960, a novel, orally available, selective inhibitor of polo-like kinase 1, shows broad-spectrum preclinical antitumor activity in multiple dosing regimens", Mol Cancer Ther., 11(3):700-9 (2012).
Hormone therapy: Cancer treatment for certain hormone-sensitive cancers, MayoClinic, http://www.riversideonline.com/health_reference/Cancer/CA00039.cfm,Accessed Jan. 22, 2014.
International Search Report for corresponding Application PCT/US/2015/013313 mailed Jul. 20, 2015.
Jimeno, et al., "Phase I study of ON 01910.Na, a novel modulator of the Polo-like kinase 1 pathway, in adult patients with solid tumors", J. Clin. Oncol., 26:5504-10 (2008).
Kluetz, et al., "Abiraterone acetate in combination with prednisone for the treatment of patients with metastatic castration-resistant prostate cancer: U.S. Food and Drug Administration drug approval summary", Clin Cancer Res., 19(24):6650-6 (2013).
Liu-Sullivan, et al., "Pooled shRNA screen for sensitizers to inhibition of the mitotic regulator polo-like kinase (PLK1)", Oncotarget, 2(12):1254-64 (2011).
Liu, et al., "Sequencing systemic therapies in metastatic castration-resistant prostate cancer", Cancer Control, 20(3):181-7 (2013).
Masiello, et al., "Bicalutamine Functions as an Androgen Receptor Antagonist by Assembly of a Transcriptionally Inactive Receptor", The JBC, 277(29):26321-26 (2002).
Mason, et al., "Functional characterization of CFI-400945, a Polo-like kinase 4 inhibitor, as a potential anticancer agent", Cancer Cell, V 26(2):163-76 (2014).
Medema, et al., "Polo-like kinase 1 inhibitors and their potential role in anticancer therapy, with a focus on NSCLC", Clin. Cancer Res., 17:6459-66 (2011).
Mross, et al., "Phase I dose escalation and pharmacokinetic study of BI 2536, a novel polo-like kinase 1 inhibitor, in patients with advanced solid tumors", J Clinical Oncology, 26(34):5511-7 (2008).
Muller-Tidow, et al., "A randomized, open-label, phase I/II trial to investigate the maximum tolerated dose of the Polo-like kinase inhibitor BI 2536 in elderly patients with refractory/relapsed acute myeloid leukaemia", Br. J. Haematol., 163(2):214-22 (2013).
Naderi and Liu, "Inhibition of androgen receptor and Cdc25A phosphatase as a combination targeted therapy in molecular apocrine breast cancer", Cancer Lett., 298: 74-87 (2010).
Noy, "Between death and survival: retinoic acid in regulation of apoptosis", Annu Rev Nutr, 30: 201-17 (2010).
Olmos, et al., "Phase I study of GSK461364, a specific and competitive Polo-like kinase 1 inhibitor, in patients with advanced solid malignancies.", Clin. Cancer Res., 17:3420-30 (2011).
Olson, "Enzalutamide plus abiraterone may have higher response rate in mCRPC than either agent alone", http://www.onclive.com/conference-coverage/ecco-esmo-2013/Enzalutamide., accessed Jan. 22, 2014.
Pasquali, et al., "Abnormal level of retinoic acid in prostate cancer tissues", The J. of Clinical Endocrinology & Metabolism, 81(6) (2013) Abstract Only.
Peeters, et al., "Mutant KRAS codon 12 and 13 alleles in patients with metastatic colorectal cancer: assessment as prognostic and predictive biomarkers of response to panitumumab", J. Clin. Oncol., 31(6):759-65 (2013).
Reddy, et al., "Discovery of a clinical stage multi-kinase inhibitor sodium (E)-2-{2-methoxy-5-[(2',4',6'-trimethoxystyrylsu-

(56) References Cited

OTHER PUBLICATIONS lfonyl)methyl]phenylamino}acetate (ON 01910.Na): synthesis, structure-activity relationship, and biological activity", J. Med. Chem., 54(18), 6254-76 (2011).

Richards, et al., "Interactions of abiraterone, eplerenone, and prednisolone with wild-type and mutant androgen receptor: a rationale for increasing abiraterone exposure or combining with MDV3100", Cancer Res., 72:2176-82 (2012).

Rudolph, et al., "BI 6727, a Polo-like kinase inhibitor with improved pharmacokinetic profile and broad antitumor activity", Clin. Cancer Res., 15(9):3094-102 (2009).

Saad, "Abiraterone slows mCRPC before chemotherapy", http://www.onclive.com/print.php?url=/publications/Oncology-live2013,Accessed Jan. 22, 2014.

Schoffski, et al., "A phase I, dose-escalation study of the novel Polo-like kinase inhibitor volasertib (BI 6727) in patients with advanced solid tumours", Eur. J. Cancer, 48(2):179-86 (2012).

Schultz, et al., "Nrf1 and Nrf2 transcription factors regulate androgen receptor transactivation in prostate cancer cells", PLoS ONE, pp. e87204 (2014).

Shapiro and Tareen, "Current and emerging treatments in the management of castration-resistant prostate cancer", Expert Rev. Anticancer Ther., 12(7):951-64 (2012).

Shi, et al., "MLN0905, a small-molecule plk1 inhibitor, induces antitumor responses in human models of diffuse large B-cell lymphoma", Mol. Cancer Thera., 11(9):2045-53 (2012).

Soifer, et al., "Direct regulation of androgen receptor activity by potent CYP17 inhibitors in prostate cancer cells", JBC, 287:3777-87 (2012).

Stadler, et al., "An open-label, single-arm, phase 2 trial of the Polo-like kinase inhibitor volasertib (BI 6727) in patients with locally advanced or metastatic urothelial cancer", Cancer, 120(7):976-82 (2014).

Steegmaier, et al., "BI 2536, a potent and selective inhibitor of polo-like kinase 1, inhibits tumor growth in vivo", Current Biology, 17:316-22 (2007).

Tanaka, et al., "HMN-176, an active metabolite of the synthetic antitumor agent HMN-214, restores chemosensitivity to multidrug-resistant cells by targeting the transcription factor NF-Y", Cancer Res., 63:6942-7 (2003).

Uckum, "Chemosensitizing anti-cancer of LFM-A13, a leflunomide metabolite analog targeting polo-like kinases", Cell Cycle, 6(24):3021-6 (2007).

Wang, et al., "Identification of retinoic acid as an inhibitor of transcription factor Nrf2 through activation of retinoic acid receptor alpha", PNAS, 19589-94 (2007).

Weissing, et al., "Targeting prostate cancer cell lines with polo-like kinase 1 inhibitors as a single agent and in combination with histone deacetylase inhibitors", FASEB J., 27(10):4279-93 (2013).

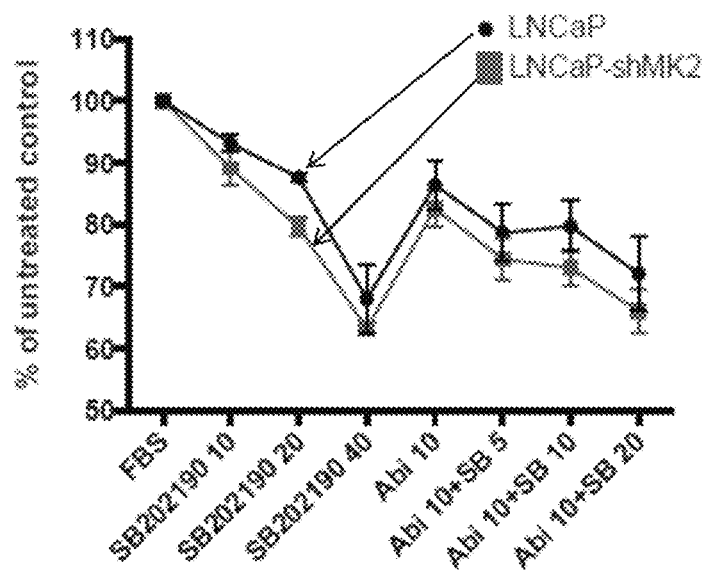
FIG. 12
*Effects of p38 inhibition on Abiraterone sensitivity in Prostate Cancer Cell lines*
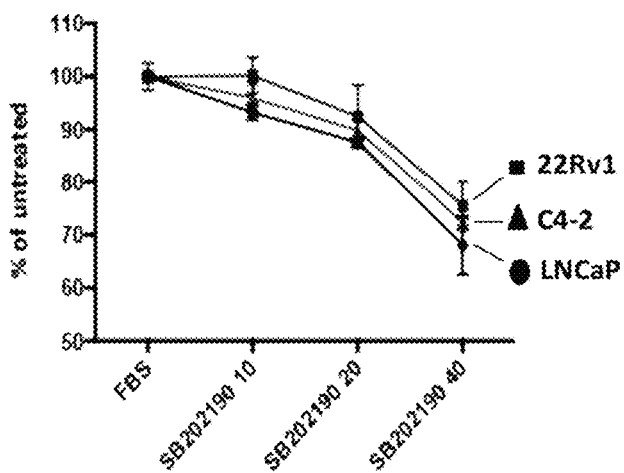
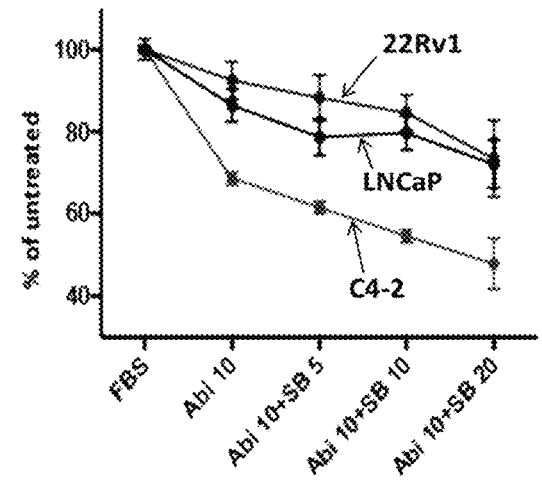
FIG. 13A  FIG. 13B

COMBINATION THERAPIES AND METHODS OF USE THEREOF FOR TREATING CANCER

This application is a continuation of U.S. Ser. No. 16/996,625, filed Aug. 18, 2020, which is a continuation of U.S. Ser. No. 16/222,459 filed Dec. 17, 2018, now U.S. Pat. No. 10,772,898, issued Sep. 15, 2020, which is a continuation of U.S. Ser. No. 15/431,312, filed Feb. 13, 2017, now U.S. Pat. No. 10,155,006, issued Dec. 18, 2018, which is a continuation of U.S. Ser. No. 14/607,732, filed Jan. 28, 2015, now U.S. Pat. No. 9,566,280, issued Feb. 14, 2017, which claims benefit of and priority to U.S. Ser. No. 61/932,283, filed on Jan. 28, 2014, which are incorporated herein in their entirety.

FIELD OF THE INVENTION

The invention is generally directed to combination therapies including an antiandrogen or androgen antagonist and a polo-like kinase inhibitor for the treatment of cancer.

BACKGROUND OF THE INVENTION

Prostate cancer is the most frequently diagnosed non-skin related cancer and the second leading cause of cancer related deaths among men. A hallmark of prostate cancer is its dependence on androgen signaling through the androgen receptor (AR). While the efficacy of androgen-depletion therapy for the treatment of metastatic prostate cancer has been known for more than 70 years, patients frequently progress to androgen-independent or castrate-resistant prostate cancer (CRPC).

Several second line anti-androgen therapies have been developed which further inhibit androgen signaling by competing with androgen for AR binding, disrupting testosterone synthesis, or both. For example, abiraterone has been shown to bind to the androgen receptor (Richards et al., *Cancer Res.*, 72:2176-2182 (2012). While beneficial, the response to these strategies is almost always short lived.

There exists a need for improved therapies that effectively treat androgen-independent or castrate-resistant prostate cancer, particularly those cancers that are not effectively treated by the second-line anti-androgen therapies discussed above.

There is also a need for therapies that effectively treat cancers which overexpress AR, or are otherwise dependent on the synthesis of steroid hormones for their growth and survival, such as some breast cancers.

Therefore, it is object of the invention to provide compositions and methods of use thereof for treating androgen-dependent cancer that have become androgen-independent or castrate-resistant.

It is also an object of the invention to provide compositions and methods of using thereof for treating cancers that overexpress AR or that are otherwise dependent on steroid hormone synthesis.

SUMMARY OF THE INVENTION

Pharmaceutical compositions containing one or more antiandrogens or androgen antagonists and one or more polo-like kinase (Plk) inhibitors and methods of making and using thereof are described herein. The antiandrogen(s) or androgen antagonist can be a steroid or a steroid-like molecule or a non-steroid. Anti-androgens or androgen antagonists, such as abiraterone, in combination with a polo-like kinase (Plk) inhibitor, such as BI2536, have shown a reduction in the viability and proliferation of cancer cells. The combination therapies can be used to improve the initial efficacy of one or the other of the active agents, or to re-sensitize cells that have become resistant to a dose (e.g., the maximum dose) of one or the other active agents when it is administered alone. Specifically, the examples show that either agent administered alone is ineffective at treating a cancer which has become hormone-desensitized while the combination is extremely effective at treating such cancers.

Pharmaceutical compositions including an effective amount of a combination of an antiandrogen or androgen antagonist and a Plk inhibitor, or combinations thereof, and methods of use thereof for treating cancer are disclosed. Typically, administration of the combination of the two active agents (i.e., antiandrogen or androgen antagonist and Plk inhibitor) is effective to reduce cancer cell proliferation or viability in a subject with cancer to a greater degree than administering to the subject the same amount of antiandrogen or androgen antagonist alone or the same amount of Plk inhibitor alone. In the most preferred embodiments, the reduction in cancer cell proliferation or viability in the subject with cancer is more than the additive reduction achieved by administering the antiandrogen or androgen antagonist alone or the Plk inhibitor alone. In some embodiments, in subjects with tumors, the combination is effective to reduce tumor burden, reduce tumor progression, or a combination thereof.

In the preferred embodiment, the antiandrogen or androgen antagonist is abiraterone or a prodrug, analog, or derivative, or pharmaceutically acceptable salt thereof. In the most preferred embodiment, the abiraterone prodrug is abiraterone acetate. The dosage of abiraterone acetate can be, for example, 250-1,500 mg.

The Plk inhibitor is preferably a Plk1 inhibitor, for example, BI2536, Volasertib (BI 6727), GSK461364, HMN-176, HMN-214, rigosertib (ON-01910), MLN0905, or Ro3280. Preferred Plk1 inhibitors include BI2536 and Volasertib. The dosage of BI25236 or Volasertib can be 1-500 mg, preferably at or below the maximum tolerated dose in a human.

These compositions and methods are particularly effective for treating prostate cancer. In some embodiments, the prostate cancer is androgen-dependent prostate cancer. In some embodiments, the prostate cancer is androgen-insensitive prostate cancer (e.g., castrate resistant prostate cancer). In some embodiments, the prostate cancer is insensitive to hormone therapy, docetaxel, abiraterone when administered alone, or one or more other first line or second line prostate cancer therapies.

These compositions and methods are also particularly effective for treating breast cancer. In preferred embodiments the breast cancer is an androgen receptor positive breast cancer. In some embodiments, the breast cancer is estrogen and/or progesterone receptor positive. In other embodiments the breast cancer is estrogen, progesterone, and androgen-receptor negative. These compositions and methods are also effective for treating non-hormonal cancers, such as pancreatic cancer, lung cancer and bowel cancer. In certain embodiments the cancers that are sensitive to additive and more than additive effects of the combination therapies are characterized by a specific gene profile. For example, cancer cells that express genes associated with the retinoic acid signaling receptor (RA) pathway can be more sensitive the effects of the combination therapies than cancer cells that do not express these genes.

Methods of treating subjects in need there using these combination therapies are also provided. The antiandrogen or androgen antagonist and the Plk inhibitor can be administered to the subject on the same day. In some embodiments, the two agents are administered simultaneously. The antiandrogen or androgen antagonist and the Plk inhibitor can be part of the same admixture, or administered as separate compositions. In some embodiments, the separate compositions are administered through the same route of administration. In other embodiments, the separate compositions are administered through different routes of administration. For example, in some embodiments, an antiandrogen or androgen antagonist, such as abiraterone acetate, is administered orally, and a Plk1 inhibitor is administered intravenously through injection or infusion.

In some embodiments, the antiandrogen or androgen antagonist is administered to the subject prior to administration of the Plk inhibitor to the subject. The antiandrogen or androgen antagonist can be administered to the subject, for example, 1, 2, 3, 4, 5, 6, 8, 10, 12, 18, or 24 hours, 1, 2, 3, 4, 5, 6, or 7 days, 1, 2, 3, or 4 weeks, or any combination thereof prior to administration of the Plk inhibitor to the subject.

In other embodiments, the Plk1 inhibitor is administered to the subject prior to administration of the antiandrogen or androgen antagonist to the subject. The Plk inhibitor can be administered to the subject, for example, 1, 2, 3, 4, 5, 6, 8, 10, 12, 18, or 24 hours, 1, 2, 3, 4, 5, 6, or 7 days, 1, 2, 3, or 4 weeks, or any combination thereof prior to administration of the antiandrogen or androgen antagonist to the subject.

In some embodiments, the combination therapy includes administering to the subject one or more additional active agents. The active agent can be a steroid, for example, prednisone which is often administered in combination with abiraterone. The second active agent can be a chemotherapeutic agent, for example, docetaxel. In some embodiments, the disclosed methods also include surgery or radiation therapy.

Methods for characterizing the gene expression profile of cancer cells and/or the tumor microenvironment have also been developed to assess the extent to which the cancer cells or tumor associated cells are sensitive to treatment with antiandrogens or androgen antagonists in combination with Plk inhibitors. These methods are useful in the diagnosis, prognosis, selection of patients, and the treatment of cancer. For example, patients having cancer cells that express components of the retinoic acid signaling pathway can be selected for treatment with the disclosed therapies. In some embodiments, the combination therapy includes methods for selecting patients who would be amenable for androgen receptor and the Plk inhibitor combination therapies, and for treating such patients.

BRIEF DESCRIPTION OF THE DRAWINGS

FIG. 9A shows the average % mitotic cells of prostate cancer cell line LNCaP following exposure to DMSO; 10 µM abiraterone; 2.5 nM Plk inhibitor BI2536; 2.5 nM Plk inhibitor BI2536/10 µM abiraterone; 1 µM docetaxel; and 1 µM docetaxel/10 µM abiraterone, respectively. FIG. 9B shows the relative change in PSA expression during abiraterone treatment as a fold-difference over PSA expression in DMSO at time points 0, 4, 8, 16, 24 and 48 hours, respectively.

FIG. 12 is a line graph, showing viability of LNCaP cells (-●-) and LNCaP-shMK2 cells (-■-) as a function of the % of untreated control in response to FBS; or varied concentrations of the p38MAPK inhibitor SB203580 (SB; 5, 10, 20 or 40 μM, respectively), in the presence or absence of 10 μM abiraterone (Abi).

FIGS. 13A and 13B are line graphs showing the effects of p38 inhibition on Abiraterone sensitivity in prostate cancer cell lines. FIG. 13A shows Cell viability (as % of untreated cells) of PCa cell lines (LNCap (-●-); 22Rv1 (-■-); and C4-2(-▲-), respectively), in response to FBS and increasing doses (10, 20 and 40 μM) of the p38MAPK inhibitor SB203580, respectively. FIG. 13B shows Cell viability (as % of untreated cells) of PCa cell lines (LNCap; 22Rv1; and C4-2, respectively), in response to increasing doses (10, 20 and 40 μM) of the p38MAPK inhibitor SB203580 (SB) with 10 μM abiraterone (Abi).

DETAILED DESCRIPTION OF THE INVENTION

I. Definitions

Figure 1:
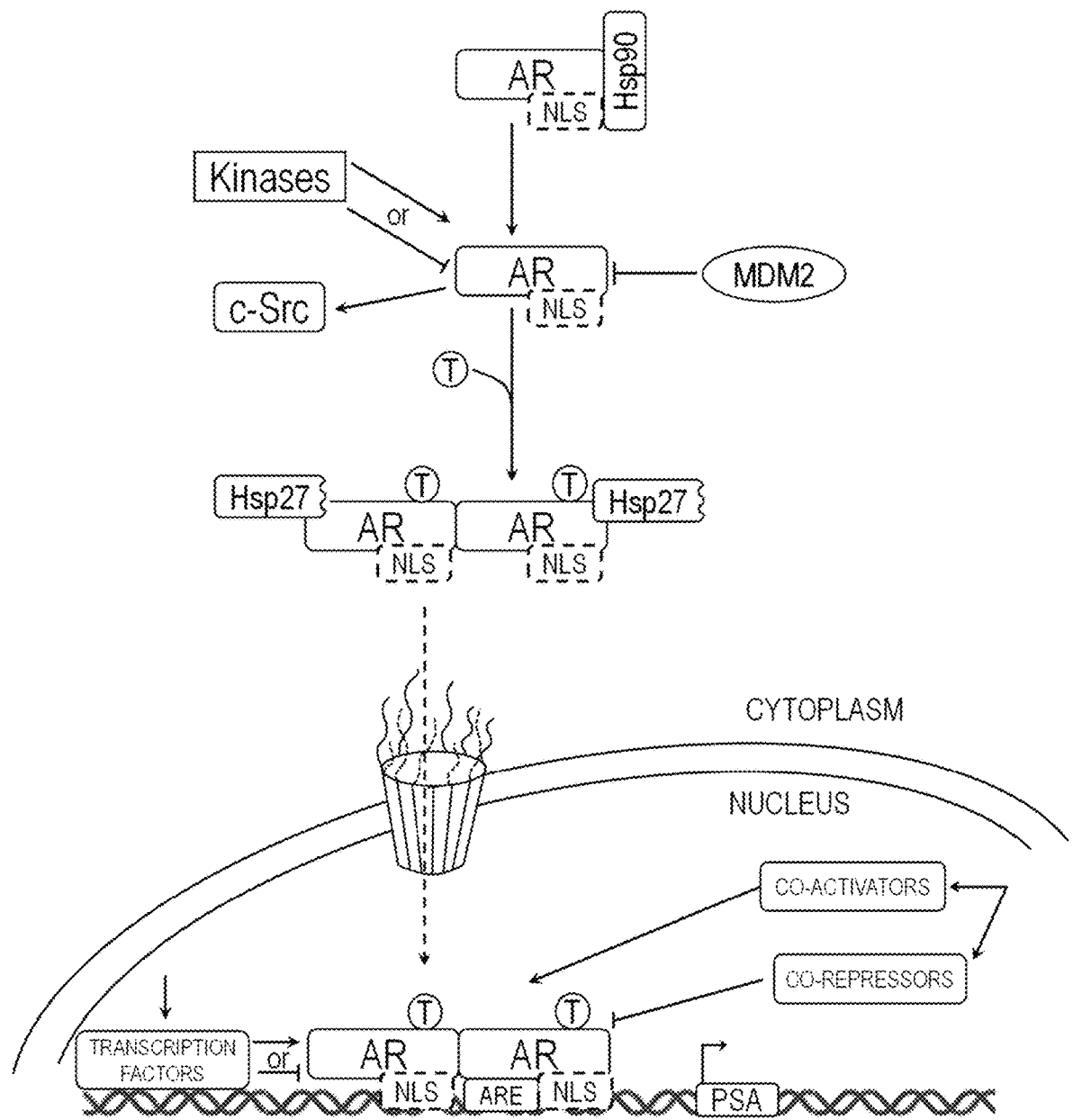
FIG. 1 is a model of androgen receptor signaling in prostate cancer. The androgen receptor (AR) is a nuclear receptor that responds to androgen (testosterone or dihydrotestosterone). Prostate cancer progresses from (1) prostate intraepithelial neoplasia, to (2) androgen-dependent prostate cancer, to (3) castrate-resistant prostate cancer (CRPC), to cancer resistant or insensitive to second line treatments such as abiraterone.

As used herein, the terms "combination therapy" refers to treatment of a disease or symptom thereof, or a method for achieving a desired physiological change, including administering to an animal, such as a mammal, especially a human being, an effective amount of two or more chemical agents or components to treat the disease or symptom thereof, or to produce the physiological change, wherein the chemical agents or components are administered together, such as part of the same composition, or administered separately and independently at the same time or at different times (i.e., administration of each agent or component is separated by a finite period of time from each other).

As used herein, the term "dosage regime" refers to drug administration regarding formulation, route of administration, drug dose, dosing interval and treatment duration.

As used herein, the terms "individual", "host", "subject", and "patient" are used interchangeably, and refer to a mammal, including, but not limited to, primates, for example, human beings, as well as rodents, such as mice and rats, and other laboratory animals.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The alkyl groups can also be substituted with one or more groups including, but not limited to, halogen, hydroxy, amino, thio, ether, ester, carboxy, oxo, and aldehyde groups. The alkyl groups may also contain one or more heteroatoms. "Lower alkyl", as used herein, means 1-6 carbons, preferably 1-5 carbons, more preferably 1-4 carbons, most preferably 1-3 carbons.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkylthio groups. "Arylthio" refers to aryl or heteroaryl groups.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and phenoxyl groups can be substituted as described above for alkyl.

The terms "amine" and "amino" are art-recognized and refer to both unsubstituted and substituted amines, e.g., a moiety that can be represented by the general formula:

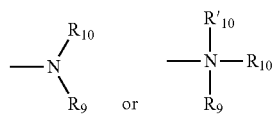

wherein, $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula:

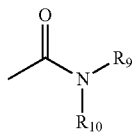

wherein, $R_9$ and $R_{10}$ are as defined above.

"Aryl" as used herein, refers to 5-, 6- and 7-membered aromatic, heterocyclic, fused aromatic, fused heterocyclic, biaromatic (e.g., biphenyl), or bihetereocyclie (e.g., bipyridinyl) ring system, optionally substituted with one or more substituents including, but not limited to, by halogen, hydroxy, nitro, cyano, amino, primary, secondary, or tertiary amino, formyl, acyl, carboxylate, alkoxy, thioether, alkyl, alkenyl, and alkynyl, cycloalkyl, etc. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 211-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Aryl" includes substituted and unsubstituted biaryl and biheteroaryl compounds, optionally interrupted or bridged by one more atoms such as carbon and/or heteroatoms (e.g., O, S, N, etc.). Examples include, but are not limited to, biaryl ethers, biaryl amines, biaryl thiols, biheteroaryl ethers, biheteroaryl amines and biheteroaryl thiols.

"Alkylaryl", as used herein, refers to an alkyl group substituted with an aryl group (e.g., an aromatic or hetero aromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, including carbon and one to four heteroatoms each selected from the group including non-peroxide oxygen, sulfur, and N(Y) wherein Y is absent or is H, O, $(C_{1-4})$ alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5- thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms including carbon and 1, 2, 3, or 4 heteroatoms each selected from the group including non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "carbonyl" is art-recognized and includes such moieties as can be represented by the general formula:

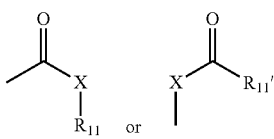

wherein, X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is a hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen; the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) which is administered in an inactive (or significantly less active) form. Once administered, the prodrug is metabolized in the body (in vivo) into the active compound.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diastereomers can be resolved or separated using techniques known in the art. "Chirality" also includes axial and planar chirality.

As used herein, the term "tumor cell" or "cancer cell", denotes a cell which may be malignant (i.e., capable of metastasis and the mediation of disease), or benign. In contrast, a "non-tumor cell" is a normal cell (which may be quiescent or activated) that is located within a tumor microenvironment, including but not limited to Tumor Infiltrating Lymphocytes (TILs), leucocytes, macrophages, and/or other cells of the immune system, and/or stromal cells, and/or fibroblasts (e.g., cancer or tumor associated fibroblasts).

The term "cell(s) of a tumor" is employed to refer to tumor cells and non-tumor cells located within a tumor or a tumor environment. The subject (e.g., patient) and the tumors to be characterized in accordance with the present disclosure may be of any mammalian species (e.g., human, or primate, canine, feline, bovine, ovine, equine, porcine, rodent species (e.g., murine), etc.). The disclosure particularly concerns the characterization of human tumor cells as well as the characterization of human tumor microenvironments. The tumor cells of relevance to the present disclosure include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochrorocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypemephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

As used herein, the term "characterizing" is intended to refer to assessing a patient, tissue sample or cell for the expression of a biomarker and its presentation on the surface of or within a cell. In accordance with the principles of the present disclosure, such characterization is mediated using molecules that physiospecifically bind, or that immunospecifically bind, to such expressed and presented molecules.

II. Compositions

The combination therapies include administration of an effective amount of at least two active agents, one being an antiandrogen or androgen antagonist and the other being a polo-like kinase inhibitor, to a subject in need thereof.

A. Active Agents

1. Antiandrogen or Androgen Antagonist

Figure 2:
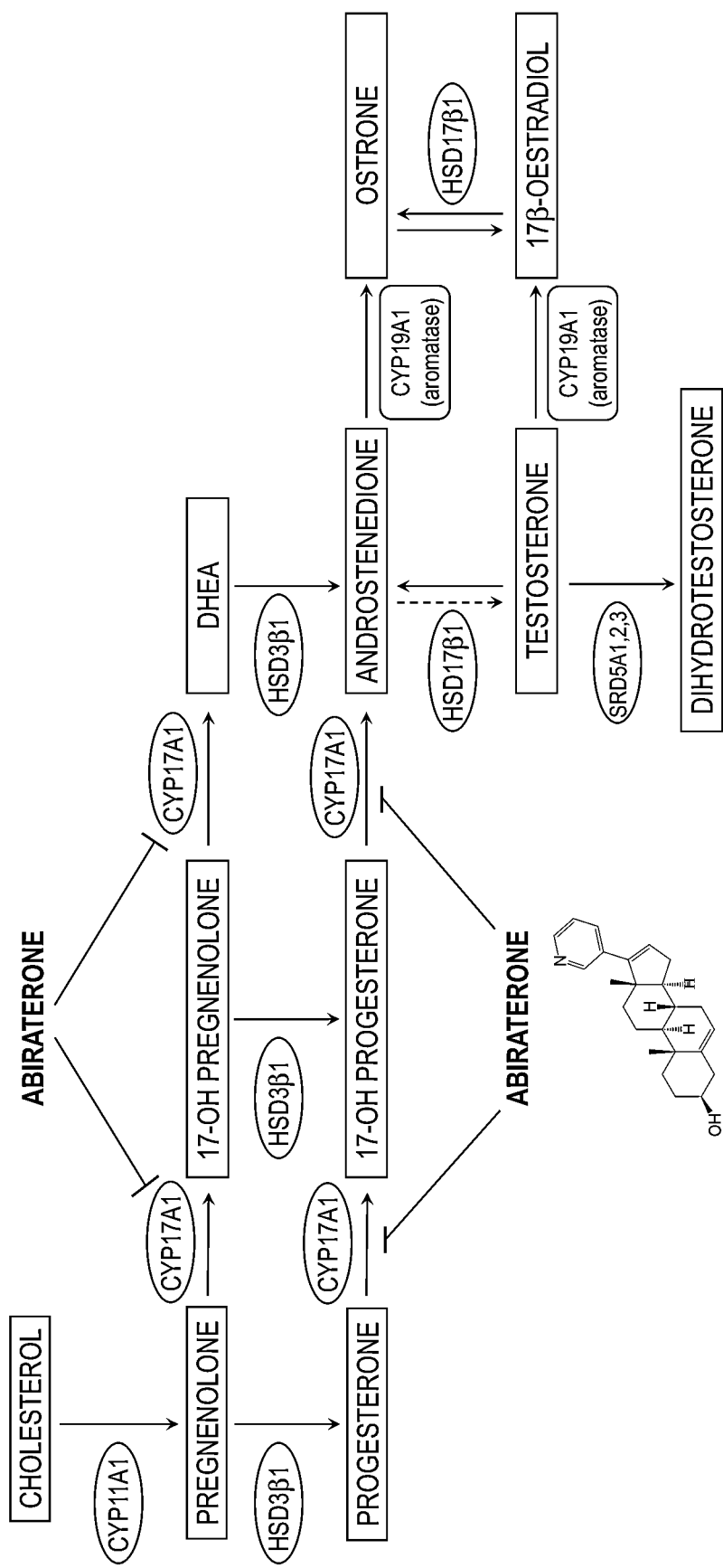
FIG. 2 is a diagram of the steps, intermediates and enzymes involved in the steroid synthesis pathway and the mechanism by which abiraterone is believed to reduce or inhibit steroid synthesis. Specifically, abiraterone acetate inhibits CYP17A1 (as shown) and also acts as a direct androgen receptor antagonist (not illustrated).

The combination therapies include an antiandrogen or androgen antagonist. The antiandrogen or androgen antagonist can reduce or inhibit the androgen synthesis pathway, or reduce or inhibit binding of endogenous ligands including, but not limited to, testosterone and dihydrotestosterone (DHT), to the androgen receptor, or a combination thereof. In preferred embodiments, the antiandrogen or androgen antagonist reduces or inhibits synthesis of testosterone or DHT. For example, the antiandrogen or androgen antagonist can reduce or inhibit the pathway at one or more steps of the steroid synthetic pathways depicted in FIG. 2. In some embodiments, the antiandrogen or androgen antagonist reduces or inhibits expression or activity of one or more enzymes or cofactors in the pathway. In a preferred embodiment, the antiandrogen or androgen antagonist reduces expression or activity of 17 alpha-hydroxylase, C17, 20-lyase, 5 alpha-reductase, or a combination thereof.

In some embodiments, the antiandrogen or androgen antagonist reduces expression or activity of the androgen receptor, reduces or inhibits ligand binding to the androgen receptor, reduces or inhibits translocation of the receptor to the nucleus, reduces or inhibits the activity of the receptor in the nucleus, or a combination thereof. For example, the antiandrogen or androgen antagonist can target the androgen receptor signaling pathway. In particular embodiments, the antiandrogen or androgen antagonist reduces or inhibits one or more of the signaling elements depicted in FIG. 1.

i. Steroidal Antiandrogen or Androgen Antagonists

In some embodiments, the antiandrogen or androgen antagonist is a steroid or has a steroidal structure, "Steroid" or "steroidal structure" as used herein typically refers to molecules having the ABCD ring characteristic of steroids.

In one embodiment, the antagonist has the formula:

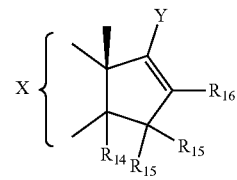

Where X represent the A, B, and C rings of a steroid, $R_{14}$ is hydrogen, $R_{15}$ is hydrogen or $C_1$-$C_6$, preferably C1-$C_4$ substituted or unsubstituted alkyl or alkoxy, hydroxy, or alkylcarbonyloxy having 2-6, preferably 2-5 carbons or $R_{14}$ and $R_{15}$ together represent a double bond, $R_{16}$ is hydrogen or C1-$C_6$, preferably $C_1$-$C_4$ substituted or unsubstituted alkyl, and Y is a substituted or unsubstituted heterocycle or fused heterocycle. In some embodiments, Y is a substituted or unsubstituted fused heterocycle.

In a particular embodiment, the antagonist is TOK-001 which has the following structure:

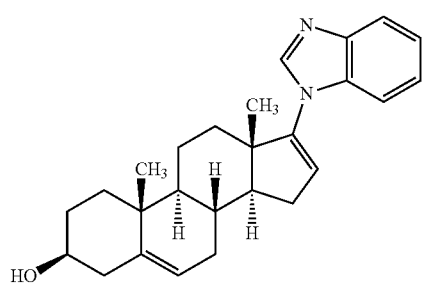

In one embodiment, the antagonist has the formula:

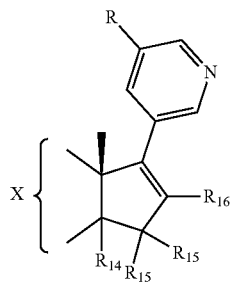

Where X represent the A, B, and C rings of a steroid, R is a hydrogen or $C_1$-$C_6$, preferably $C_1$-$C_4$ substituted or unsubstituted alkyl, $R_{14}$ is hydrogen, $R_{15}$ is hydrogen or $C_1$-$C_6$, preferably $C_1$-$C_4$ substituted or unsubstituted alkyl or alkoxy, hydroxy, or alkylcarbonyloxy having 2-6, preferably 2-5 carbons or $R_{14}$ and $R_{15}$ together represent a double bond, and $R_{16}$ is hydrogen or $C_1$-$C_6$, preferably $C_1$-$C_4$ substituted or unsubstituted alkyl.

In the most preferred embodiments, the antiandrogen or androgen antagonist is abiraterone, or a prodrug, analog, or derivative, or pharmaceutically acceptable salt thereof. The structure of abiraterone is shown below:

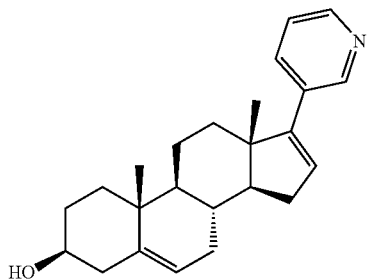 [SMILES: C[C@]12CC[C@H](O)CC1=CC[C@@H]1[C@@H]2CC[C@]2(C)C(c3cccnc3)=CC[C@@H]12]

Abiraterone, as well as prodrugs, analogs, derivatives, or pharmaceutically acceptable salts thereof are known in the art. See, for example, U.S. Pat. No. 5,604,213 which is specifically incorporated by reference herein in its entirety.

Abiraterone inhibits 17 α-hydroxylase/C17,20 lyase (CYP17A1), an enzyme which is expressed in testicular, adrenal, and prostatic tumor tissues. CYP17 catalyzes two sequential reactions: (a) the conversion of pregnenolone and progesterone to their 17-α-hydroxy derivatives by its 17 α-hydroxylase activity, and (b) the subsequent formation of dehydroepiandrosterone (DHEA) and androstenedione, respectively, by its C17,20 lyase activity (see FIG. 2). DHEA and androstenedione are androgens and precursors of testosterone, therefore, inhibition of CYP17 activity by abiraterone decreases circulating levels of testosterone. It is also believed that abiraterone acts as a direct androgen receptor antagonist.

Suitable dosages of abiraterone when used as a first or second line therapy for treatment of cancer are also known in the art. For example, U.S. Pat. No. 5,604,213 teaches that a therapeutically effective dose can be in the range 0.001-0.04 mmole/kg body weight, preferably 0.001-0.01 mmole/kg, administered daily or twice daily during the course of treatment. In some embodiments the dosage is 10-2,000 mg/patient per day, 100-1,500 mg/patient per day, 250-1,250 mg/patient per day, or 500-1000 mg/patient per day.

In a particular embodiment, the abiraterone is formulated as a prodrug such as abiraterone acetate. Following administration, abiraterone acetate is converted into the active form, abiraterone. It is believed this conversion is esterase-mediated and not dependent on CYP. Abiraterone acetate is a lipophilic compound with an octanol-water partition coefficient of 5.12 (Log P) and is practically insoluble in water. Abiraterone acetate is sold under the trade name ZYTIGA®. A tablet for oral administration includes 250 mg abiraterone acetate and inactive ingredients including colloidal silicon dioxide, croscarmellose sodium, lactose monohydrate, magnesium stearate, microcrystalline cellulose, povidone, and sodium lauryl sulfate. The recommend daily dosage is 1000 mg per day (e.g., four tablets of ZYTIGA®), but can be increased or decreased depending on the condition of the subject to be treated. For example, the dosage or dosing frequency is often decreased (e.g., to 250 mg/day, 500 mg/day, 750 mg/day, etc.) if the subject is experiencing hepatotoxicity, or when the drug is coadministered with a CYP2D6 substrate. Alternatively, the dosage or dosing frequency can be increased when administered in combination with a strong CYP3A4 inducer.

For the treatment of prostate cancer, abiraterone is often administered in combination with a steroid such as prednisone or prednisolone. The steroid is given to reduce the chances of (1) fluid retention, (2) raised blood pressure, or (3) decreased levels of potassium in the blood as a result of the abiraterone treatment. Suitable prednisone compositions and dosages for use in combination with abiraterone are known in the art. For example, a recommended prednisone co-therapy is 5 mg administered orally twice daily.

ii. Non-Steroidal Antidrogens and Androgen Antagonists

In some embodiments, the antiandrogen or androgen antagonist is not a steroid or does not have a steroidal structure. In one embodiment, the compound has the structure:

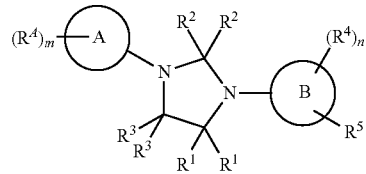

wherein,
ring A is monocyclic heteroaryl, bicyclic heteroaryl, or naphthyl;
m is 0, 1, 2, 3 or 4;
each $R^4$ is independently selected from H, halogen, —CN, —$NO_2$, —OH, —$OR^9$, —$SR^9$, —S(=O)$R^{10}$, —S(=O)$_2R^{10}$, —N($R^{11}$)S(=O)$_2R^{10}$, —S(=O)$_2$N($R^9$)$_2$, —C(=O)R°, —OC(=O)$R^{10}$, —$CO_2R^9$, —N($R^9$)$_2$, substituted or unsubstituted $C_1$-$C_6$alkyl, substituted or unsubstituted $C_1$-$C_6$ fluoroalkyl, substituted or unsubstituted $C_1$-$C_6$ fluoroalkoxy, substituted or unsubstituted $C_1$-$C_6$ alkoxy, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted phenyl or substituted or unsubstituted monocyclic heteroaryl;

each $R^1$ is independently selected from H, —OH, substituted or unsubstituted $C_1$-$C_6$ alkyl, substituted or unsubstituted $C_1$-$C_6$ alkoxy, and substituted or unsubstituted $C_1$-$C_6$ fluoroalkyl;

or both $R^1$ are taken together with the carbon atom to which they are attached to form a substituted or unsubstituted $C_3$-$C_{10}$ cycloalkyl or a substituted or unsubstituted $C_2$-$C_{10}$ heterocycloalkyl;

each $R^2$ is H; or both $R^2$ are taken together with the carbon to which they are attached to form —C(=S)— or —C(=O)—;

each $R^3$ is H; or both $R^3$ are taken together with the carbon to which they are attached to form —C(=S)— or —C(=O)—; provided that each $R^2$ is not H if each $R^3$ is H;

ring B is phenyl, naphthyl, monocyclic heteroaryl, or bicyclic heteroaryl;

n is 0, 1, 2, 3 or 4;

each $R^4$ is independently selected from H, halogen, —CN, —$NO_2$, —OH, —$OR^9$, —$SR^9$, —S(=O)$R^{10}$, —S(=O)$_2$$R^{10}$, —N($R_{11}$)S(=O)$_2$$R^{10}$, —S(=O)$_2$N($R^9$)$_2$, —C(=O)$R^{10}$, —OC(=O)$R^{10}$, —$CO_2$$R^9$, —$OCO_2$$R^{10}$, —N($R^9$)$_2$, —C(=O)N($R^9$)$_2$, —OC(=O)N($R^9$)$_2$, —$NR^{11}$C(=O)N($R^9$)$_2$, —$NR^{11}$C(=O)$R^{10}$, —$NR^{11}$C(=O)$OR^{10}$, substituted or unsubstituted $C_1$-$C_6$ alkyl, substituted or unsubstituted $C_1$-$C_6$ fluoroalkyl, substituted or unsubstituted $C_1$-$C_6$ fluoroalkoxy, substituted or unsubstituted $C_1$-$C_6$ alkoxy, and substituted or unsubstituted $C_1$-$C_6$ heteroalkyl;

$R^5$ is substituted or unsubstituted $C_2$-$C_{10}$ alkyl, substituted or unsubstituted $C_2$-$C_{10}$ fluoroalkyl, substituted or unsubstituted $C_2$-$C_{10}$ alkoxy, substituted or unsubstituted $C_2$-$C_{10}$ fluoroalkoxy, substituted or unsubstituted $C_2$-$C_{10}$ heteroalkyl, substituted or unsubstituted $C_2$-$C_{10}$ heterofluoroalkyl, or -$L^1$-$L^2$-$R^6$;

$L^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

$L^2$ is substituted or unsubstituted $C_1$-$C_6$ alkylene, substituted or unsubstituted $C_1$-$C_6$ fluoroalkylene or substituted or unsubstituted $C_1$-$C_6$ heteroalkylene;

$R^6$ is —CN, —$NO_2$, —OH, —$OR^9$, —$SR^9$, —S(=O)$R^{10}$, —S(=O)$_2$$R^{10}$, —N($R_{11}$)S(=O)$_2$$R^{10}$, —S(=O)$_2$N($R^9$)$_2$, —C(=O)$R^{10}$, —OC(=O)$R^{10}$, —$CO_2$$R^9$, —$OCO_2$$R^{10}$, —N($R^9$)$_2$, —C(=O)N($R^9$)$_2$, —OC(=O)N($R^9$)$_2$, —$NR^{11}$C(=O)N($R^9$)$_2$, —$NR^{11}$C(=O)$R^{10}$, —$NR^{11}$C(=O)$OR^{10}$, substituted or unsubstituted $C_1$-$C_6$alkyl, substituted or unsubstituted $C_1$-$C_6$ fluoroalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_{10}$ cycloalkyl, substituted or unsubstituted $C_2$-$C_{10}$ heterocycloalkyl, substituted or unsubstituted aryl, substituted or unsubstituted heteroaryl, $C_1$-$C_4$ alkylene-(substituted or unsubstituted $C_3$-$C_{10}$ cycloalkyl), —$C_1$-$C_4$ alkylene-(substituted or unsubstituted $C_3$-$C_{10}$ heterocycloalkyl), —$C_1$-$C_4$ alkylene-(substituted or unsubstituted aryl), and —$C_1$-$C_4$ alkylene-(substituted or unsubstituted heteroaryl); or two $R^9$ groups attached to the same N atom are taken together with the N atom to which they are attached to form a substituted or unsubstituted $C_2$-$C_{10}$ heterocycloalkyl;

$R^{10}$ is substituted or unsubstituted $C_1$-$C_6$ alkyl, substituted or unsubstituted $C_1$-$C_6$ heteroalkyl, substituted or unsubstituted $C_1$-$C_6$ fluoroalkyl, a substituted or unsubstituted $C_3$-$C_{10}$ cycloalkyl, a substituted or unsubstituted $C_2$-$C_{10}$ heterocycloalkyl, a substituted or unsubstituted aryl, a substituted or unsubstituted benzyl, a substituted or unsubstituted heteroaryl, —$C_1$-$C_4$ alkylene-(substituted or unsubstituted $C_3$-$C_{10}$ cycloalkyl), —$C_1$-$C_4$ alkylene-(substituted or unsubstituted $C_2$-$C_{10}$ heterocycloalkyl), —$C_1$-$C_4$alkylene-(substituted or unsubstituted aryl), or —$C_1$-$C_4$ alkylene-(substituted or unsubstituted heteroaryl);

$R^{11}$ is H or $C_1$-$C_4$ alkyl.

These compounds are described in U.S. Patent Application Publication No. 2013/0116258, which is incorporated herein by reference in its entirety.

In some embodiments, the compound is ARN-509 which has the following structure:

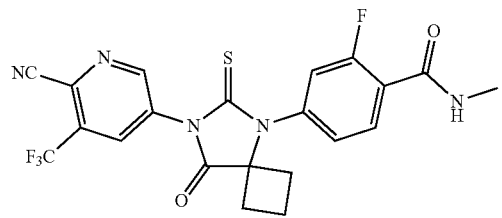

ARN-509

2. Polo-Like Kinase Inhibitor

The combination therapies include one or more polo-like kinase (Plk) inhibitors. Polo-like kinases (Plks) are a family of conserved serine/threonine kinases involved in the regulation of cell cycle progression through G2 and mitosis. The catalytic domain of polo-like kinases is located in the N-terminus. The C-terminus of Plks contains one or two motifs known as polo boxes that help localize the kinase to specific mitotic structures during mitosis. These include the centrosomes in early M phase, the spindle midzone in early and late anaphase and the midbody during cytokinesis.

Mammalian polo-like kinases include Plk1, Plk2/Snk, Plk3/Prk/FnK, Plk4/Sak, and Plk5. The polo-like kinase inhibitor can reduce or inhibit expression or activity of Plk1, Plk2/Snk, Plk3/Prk/FnK, Plk4/Sak, and Plk5. For example, in some embodiments the inhibitor reduces or inhibits Plk1, Plk2/Snk, Plk3/Prk/FnK, Plk4/Sak, and/or Plk5 mRNA or protein expression. In some embodiments, the polo-like kinase inhibitor reduces or inhibits the kinase activity of Plk1, Plk2/Snk, Plk3/Prk/FnK, Plk4/Sak, and/or Plk5. In some embodiments, the polo-like kinase inhibitor reduces or inhibits expression of more than one polo-like kinase, for example by targeting a conserves region of the proteins such as the polo box(es).

a. Small Molecule PLK Inhibitors

In a preferred embodiment, the polo-like kinase inhibitor (Plk inhibitor) is a small molecule. "Small molecule" as used herein, refers to an organic molecule, inorganic molecule, or organometallic molecule having a molecular weight less than 2000, 1500, 1200, 1000, 750, or 500 atomic mass units.

Polo-like kinase inhibitors are known in the art and include, for example, BI2536, Volasertib (BI 6727), GSK461364, HMN-176, HMN-214, rigosertib (ON-01910), MLN0905, and Ro3280, several of which are discussed in Medema, et al., *Clin. Cancer Res.*, 17:6459-6466 (2011), which is specifically incorporated by reference herein in its entirety.

Each of the Plk inhibitors, preferred dosages and routes of administration are discussed in more detail below, however, generally, the compounds can be administered to humans in an amount from about 0.0001 mg/kg of body weight to about 100 mg/kg of body weight per day. Generally, for intravenous injection or infusion, dosage may be lower than for other methods of delivery.

Some of the Plk inhibitors have been investigated for anti-cancer properties in preclinical experiments and clinical trials. In some embodiments, the dosage of Plk inhibitor used in combination therapies is the same as a dosage used to treat or prevent a cancer in a clinical trial, or a human equivalent to a dosage used to treat cancer in an animal study. However, the Examples below illustrate that the more than additive effect of the combination therapy is not the result of G2/M arrest induced by the Plk inhibitor. Therefore, in some embodiments, the dosage is different than the dosage used to treat cancer. For example, the dosage can be lower than the dosage used to treat cancer, or the dosage can be higher than the dosage used to treat cancer provided that the dosage is safe and tolerable to the subject. Preferably, the dosage is at or below a maximum tolerated dose as determined in a clinical trial. In some embodiments, the maximum tolerated dose is 250 mg.

i. Dihydropteridinones

In some embodiments, the Plk inhibitor has the formula described in U.S. Pat. No. 6,806,272, which is incorporated herein reference in its entirety. The compounds have the formula:

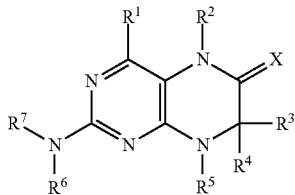

wherein $R^1$ denotes a group selected from among hydrogen, $NH_2$, XH, halogen and a $C_1$-$C_3$-alkyl group optionally substituted by one or more halogen atoms, $R_2$ denotes a group selected from among hydrogen, CHO, XH, —X—$C_1$-$C_2$-alkyl and an optionally substituted $C_1$-$C_3$-alkyl group, $R^3$, $R^4$ which may be identical or different denote a group selected from among optionally substituted $C_1$-$C_{10}$-alkyl, $C_2$-$C_{10}$-alkenyl, $C_2$-$C_{10}$-alkynyl, aryl, heteroaryl, $C_3$-$C_8$-cycloalkyl, $C_3$-$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl and —$NR^8$-heterocycloalkyl, or a group selected from among hydrogen, halogen, $COXR^8$, $CON(R^8)_2$, $COR^8$ and $XR^8$, or $R^3$ and $R^4$ together denote a 2- to 5-membered alkyl bridge which may contain 1 to 2 heteroatoms, $R^5$ denotes hydrogen or a group selected from among optionally substituted $C_3$-$C_{10}$-alkyl, $C_2$-$C_{10}$-alkenyl, $C_2$-$C_{10}$-alkynyl, aryl, heteroaryl and —$C_3$-$C_6$-cycloalkyl, or $R^3$ and $R^5$ or $R^4$ and $R^5$ together denote a saturated or unsaturated $C_3$-$C_4$-alkyl bridge which may contain 1 to 2 heteroatoms, $R^6$ denotes optionally substituted aryl or heteroaryl, $R^7$ denotes hydrogen or —CO—X—$C_1$-$C_4$-alkyl, and X in each case independently of one another denotes O or S, $R^8$ in each case independently of one another denotes hydrogen or a group selected from among optionally substituted $C_1$-$C_4$-alkyl, $C_2$-$C_4$-alkenyl, $C_2$-$C_4$ alkynyl and phenyl, optionally in the form of the tautomers, the racemates, the enantiomers, the diastereomers and the mixtures thereof, and optionally the pharmacologically acceptable acid addition salts thereof.

Specific compounds of the formula above and other Plk inhibitors are described below.

BI2536

In a preferred embodiment, the Plk inhibitor is BI2536, or a prodrug, analog, or derivative, or pharmaceutically acceptable salt thereof. BI2536 has the structure:

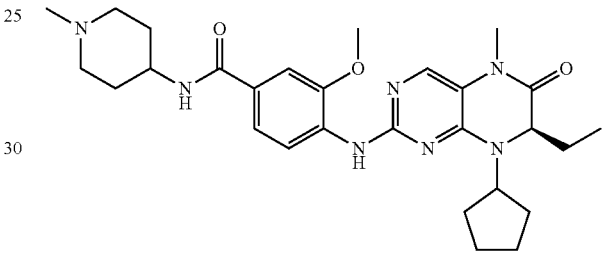

BI2536 is a potent Plk1 inhibitor with 1050 of 0.83 nM (Steegmaier, et al., *Current Biology*, 17:316-322 (2007)). It shows 4- and 11 fold greater selectivity against Plk2 and Plk3. In preclinical experimental, BI2536 was given i.v. once or twice per week was highly efficacious in diverse xenograft models with acceptable tolerability. The drug was believed to work by inhibiting cell proliferation through a mitotic arrest, and subsequently induction of tumor-cell death. Administration of BI2536 at 50 mg/kg once or twice per week significantly inhibited growth of HCT 116 xenografts with T/C of 15% and 0.3%, respectively, BI2536 treatment twice-weekly also lead to excellent tumor-growth in BxPC-3 and A549 models with T/C of 5% and 14%, respectively ((Steegmaier, et al., *Current Biology*, 17:316-322 (2007)).

BI2536 has been the subject of a number of clinical travels testing the safety and efficacy of the drug in a range of dosages and regimes and for treatment of a number of cancers. For example, in a randomized, open-label, phase I/II trial to investigate the maximum tolerated dose of the Polo-like kinase inhibitor BI2536 in elderly patients with refractory/relapsed acute myeloid leukemia, 68 elderly patients with relapsed/refractory AML were administered BI2536 on one of three schedules (day 1, days 1-3, and days 1+8). The maximum tolerated dose was 350 mg and 200 mg in the day 1 and days 1+8 schedules, respectively. The day 1-3 schedule appeared equivalent to the day 1 schedule and was discontinued early (Muller-Tidow, et al., *Br. J. Haematol.*, 163(2):214-22 (2013)). Likewise, a phase I open-label dose-escalation study tested the maximum tolerated dose of intravenous BI2536 together with pemetrexed in previously treated patients with non-small-cell lung cancer. The patients received 500 mg/m² pemetrexed and escalating doses of BI2536 on day 1 every 3 weeks. Forty-one patients received BI2536 (100-325 mg). Two dose-limiting toxicities (DLT) occurred at 1312536 325 mg (grade 3 pruritus and rash; grade 4 neutropenia). Therefore, the maximum tolerated dose (MTD) for BI2536 in combination with pemetrexed was 300 mg (Ellis, et al., *Clin. Lung Cancer*, 14(1): 19-27 (2013) Epub 2012 June 1). BI2536 at 200 mg combined with standard-dose pemetrexed was determined to have an acceptable safety profile. Other studies have suggested a lower MTD, e.g., 50-70 mg (Frost, et *Curr. Oncology*, 19(1):e25-35 (2012)).

An open, randomized, clinical phase II trial in patients with un-resectable advanced pancreatic cancer investigating the efficacy, safety, and pharmacokinetics of BI 2536 administered in repeated 3-week cycles as a single i.v. dose of 200 mg on day 1 or as 60 mg doses on days 1, 2, and 3 is currently underway.

Therefore, in some embodiments, BI2536 is administered to a subject 1, 2, 3, or more times a week in a dosage of about 1-500 mg, preferably about 10-400 mg, more preferably about 50-350 mg, most preferably 60-300 mg. In a particular embodiment the dosage is 50, 100, 150, 200, 250, 300, or 350 mg of BI2536 administered to a subject once, twice, three times or more than three times a week, or once every two, three or four weeks. In some embodiments, BI2536 is administered by intravenous injection or infusion.

Volasertib (BI6727)

Like BI2536, BI6727 is an ATP-competitive kinase inhibitor from the dihydropteridinone class of compounds. BI6727 is a highly potent Plk1 inhibitor with IC50 of 0.87 nM. It also shows 6- and 65-fold greater selectivity against Plk2 and Plk3. BI6727 at concentrations up to 10 μM displays no inhibitory activity against a panel of >50 other kinases in vitro (Rudolph D, et al. *Clin. Cancer Res.*, 15(9), 3094-3102 (2009)). BI6727 has the structure:

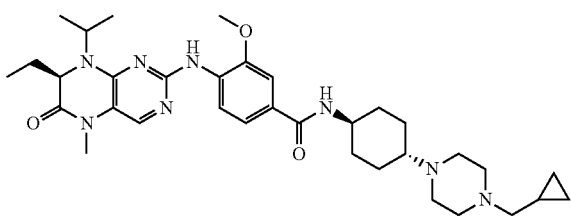 [SMILES: CC[C@@H]1C(=O)N(C)c2cnc(Nc3ccc(C(=O)N[C@H]4CC[C@H](N5CCN(CC6CC6)CC5)CC4)cc3OC)nc2N1C(C)C]

Preclinical experiments in a mouse model show that administration of BI6727 at ~25 mg/kg/day significantly inhibits the growth of multiple human carcinoma xenografts including HCT 116, NCI-H460, and taxane-resistant CXB1 colon carcinoma, accompanied by an increase in the mitotic index as well as an increase in apoptosis (Rudolph D, et al. *Clin. Cancer Res.*, 15(9), 3094-3102 (2009)). Some in vivo studies indicate that BI6727 exhibits a better toxicity and pharmacokinetic profile than BI2536 (Harris, et al., *BMC Cancer*, 12, 80 (2012)).

BI6727 has been the subject of a number of clinical travels testing the safety and efficacy of the drug in a range of dosages and regimes and for treatment of a number of cancers. A phase I first-in-humans study of volasertib was conducted in 65 patients with advanced solid tumors, including 10 with NSCLC. Volasertib was administered i.v. once every 3 weeks following a dose-escalation design (12-450 mg). The study reported neutropenia, thrombocytopenia, and febrile neutropenia as DLTs and an MTD of 400 mg (Gil, et al., *J. Clin. Oncol.*, 28 Suppl 15:abstr 3061 (2010), Schoffski, et al., *Eur. J. Cancer*, 48(2):179-86 (2012)). 300 mg was the recommended dose for further development based on overall tolerability. In a phase I study of volasertib (DI 6727) combined with afatinib (BIBW 2992) in advanced solid tumors, the MTD was determined to be 300 mg of DI 6727, when administered in combination with afatinib (Peeters, et al., *J. Clin. Oncol.*, 31 (suppl; abstr 2521) (2013)).

Therefore, in some embodiments, BI 6727 is administered to a subject 1, 2, 3, or more times a week in a dosage of between about 1-600 mg, preferably about 10-500 mg, more preferably about 50-400 mg, most preferably 100-350 mg. In a particular embodiment the dosage is 50, 100, 150, 200, 250, 300, 350, or 400 mg of BI 6727 administered to a subject once, twice, three times or more than three times a week, or once every two, three or four weeks. In some embodiments, BI 6727 is administered by intravenous injection or infusion.

ii. Other Classes of Plk Inhibitors

The inhibitor may be a molecule other than a dihydropteridinones. Other classes of inhibitors include, but are not limited to, pyridopyrimidines (see U.S. Patent Application Publication No. 2010/004141 and WO 2009/112524), aminopyrimidines (see U.S. Patent Application Publication No. 2010/010014), substituted thiazolidinones (see European Patent Application No. EP 2141163), pteridine derivatives (see European Patent Application No. EP 2079743), dihydroimidazo[1,5-f]pteridines (see WO 2010/025073), meta-substituted thiazolidinones, (see U.S. Patent Application Publication No. 2010/048891), benzyl styryl sulfone analogues (see WO 2009/128805), and stilbene derivatives.

The applications cited above are incorporated herein by reference in their entirety.

Specific inhibitors are discussed below:

GSK461364

GSK461364 inhibits purified Plk1 with Ki of 2.2 nM. It is more than 1000-fold selective against Plk2/3.

The structure for GSK461364 is

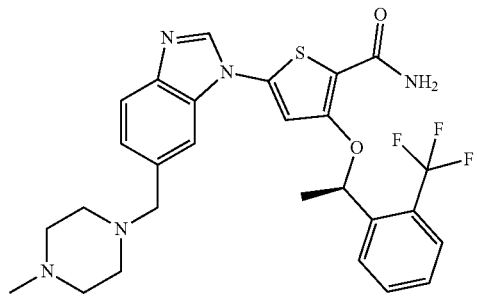 [SMILES: C[C@@H](Oc1cc(-n2cnc3ccc(CN4CCN(C)CC4)cc32)sc1C(N)=O)c1ccccc1C(F)(F)F]

Cell culture growth inhibition by GSK461364 can be cytostatic or cytotoxic but leads to tumor regression in xenograft tumor models under proper dose scheduling. In an animal model, dosages of 25, 50, and 100 mg/kg were administered via i.p. every 2 days or every 4 days (Gilmartin, et al., *Cancer Res*, 69(17), 6969-6977 (2009)).

A phase I first-in-humans study of GSK461364 was conducted in 27 patients with advanced solid tumors (Ohms, et al., *Clin. Cancer Res.*, 17:3420-30 (2011)). The agent was administered i.v. following 2 schedules with different dosing (50-225 mg on days 1, 8, and 15 (schedule A) or 25-100 mg on days 1, 2, 8, 9, 15, and 16 (schedule B) on a 28-day cycle. DLTs included grade 4 neutropenia, sepsis, and pulmonary embolism. The final recommended phase II dose for GSK461364 was 225 mg administered intravenously in schedule A. Because of the high incidence (20%) of venous thrombotic emboli (VIE), coadministration of prophylactic anticoagulation agent is recommended.

Therefore, in some embodiments, GSK461364 is administered to a subject 1, 2, 3, or more times a week in a dosage of between about 1-400 mg, preferably about 10-350 mg, more preferably about 25-300 mg, most preferably 25-225 mg. In a particular embodiment the dosage is 50, 100, 150, 200, 250, 300, 350, or 400 mg of GSK461364 administered to a subject once, twice, three times or more than three times a week, or once every two, three or four weeks. In some embodiments, GSK461364 is administered by intravenous injection or infusion.

HMN 176 and HMN-214

HMN-176 is a stilbene derivative that is an active metabolite of the prodrug HMN-214. It does not directly inhibit the enzymatic activity of Plk1 but rather affects subcellular distribution of Plk1. The structures of HMN-176 and HMN-214 are (A) and (B) respectively:

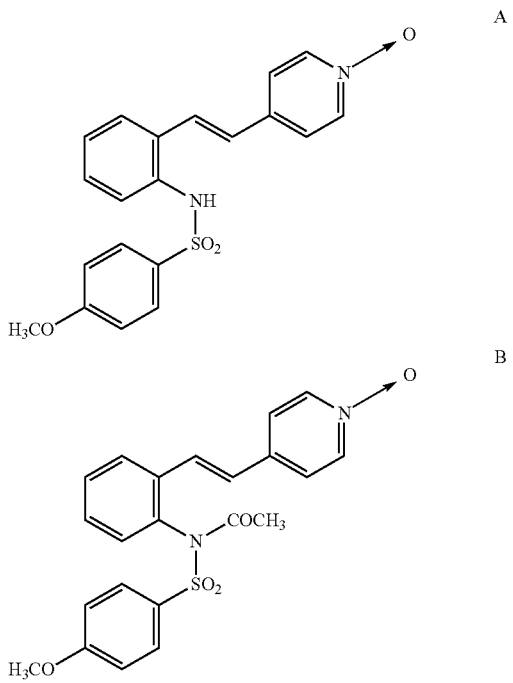

HMN-176 shows potent cytotoxicity toward various human tumor cell lines, and in mitotic cells, it causes cell cycle arrest at M phase through the destruction of spindle polar bodies, followed by the induction of DNA fragmentation. In preclinical experiments it was a potent antitumor activity in mouse xenograft models when administered at dosage of 10 mg/kg and 20 mg/kg on days 1 and 28 (Tanaka, et al., *Cancer Res.*, 63:6942-6947 (2003).

A phase I pharmacokinetic study of HMN-214 in patients with advanced solid tumors, thirty-three patients were enrolled onto four dosing cohorts of HMN-214 from 3 to 9.9 mg/m$^2$/d using a continuous 21-day dosing schedule every 28 days. A severe myalgia/bone pain syndrome and hyperglycemia were dose-limiting toxicities at 9.9 mg/m$^2$/d, and the maximum tolerated dose and recommended dose on this schedule was determined to be 8.0 mg/m$^2$/d (Garland, et al., *Clin. Cancer Res.*, 1; 12(17):5182-9 (2006)).

In another study, DLTs of prolonged neutropenia, febrile neutropenia, neutropenic sepsis, electrolyte disturbance, neuropathy, and myalgia were observed at doses of 24 to 48 mg/m$^2$ for 5 consecutive days every 4 weeks. MTD was established at the range of 18 to 30 mg/m$^2$, based on previous patient treatment load (Patnaik, *J. Clin. Oncol.*, 22 Suppl:abstr 514.).

Therefore, in some embodiments, HMN-214 (or HMN-176) is administered to a subject 1, 2, 3, 4, 5, 6, or 7 times a week in a dosage of between about 1-100 mg/m$^2$, preferably about 2.5-50 mg/m$^2$, more preferably about 3-40 mg/m$^2$, most preferably 7.5-30 mg/m$^2$. In a particular embodiment the dosage is 1, 2, 3, 4, 5, 6, 7, 8, 9, or 10 mg/m$^2$ of HMN-214 (or HMN-176) administered to a subject once, twice, three times or more than three times a week, for example, on days 1-21 of a 28 day cycle. In another particular embodiment the dosage is 10 to 48 mg/m$^2$ preferably 18 to 30 mg/m$^2$ of HMN-214 (or HMN-176) administered once, twice, three times or more than three times a week, for example, days 1-5 of a 28 day cycle. In some embodiments, HMN-214 (or HMN-176) is administered orally.

Rigosertib (ON-01910)

The benzyl styryl sulfone analogue ON 01910 is an ATP-noncompetitive, multitargeted inhibitor of several tyrosine kinases and cyclin-dependent kinase 1 (Cdk1; IC50=18-260 nmol/L). It is reported to have a particularly strong potency (IC50=9-10 nmol/L) toward Plk1 (Gumireddy, et al., *Cancer Cell*, 7:275-86 (2005)). The structure of ON-01910 is

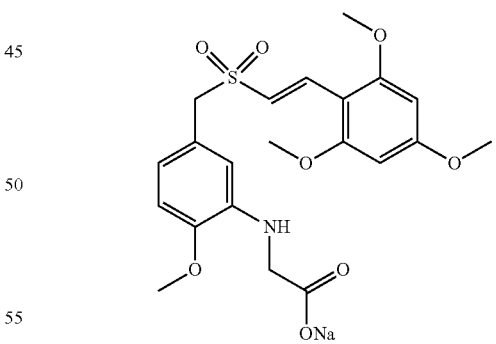

In preclinical animal studies in mouse xenograft models of Bel-7402, MCF-7, and MIA-PaCa cells, Rigosertib (250 mg/kg) inhibited tumor growth and (200 mg/kg) showed inhibition of tumor growth in a mouse xenograft model of BT20 cells (Gumireddy, et al., *Cancer Cell*, 7:275-86 (2005), Reddy, et al., *J Med. Chem.*, 54(18), 6254-6276 (2011)).

A phase I first-in-humans study of ON 01910 was conducted in 20 patients with advanced solid tumors (none with NSCLC). The agent was administered i.v. at 80 to 4,370 mg by accelerated titration design on days 1, 4, 8, 11, 15, and 18 in 28-day cycles (Jimeno, et al., *J Clin. Oncol.*, 26:5504-10 (2008). Grade 3 abdominal pain was reported as a DLT at an MTD of 3,120 mg.

In a clinical trial testing the safety and pharmacokinetics of oral on 01910 in patients with myelodysplastic syndrome, ON 01910 was given twice a day up to 14 days at doses escalating from 70 mg to 700 mg.

Therefore, in some embodiments, ON 01910 is administered to a subject 1, 2, 3 or more days a week in a dosage of about 50-6,000 mg, preferably about 60-4,500 mg, more preferably about 150 mg-1,500 mg once daily, or 75-750 mg twice daily. In particular embodiments, ON 01910 administered to a subject once, twice, three times or more than three times a week, or once every two, three or four weeks. In a specific embodiment, the drug is administered every day for 14 days. In some embodiments, ON 01910 is administered by intravenous injection or infusion.

MLN0905

MLN0905 is a potent inhibitor of PLK1 with IC50 of 2 nM. MLN0905 inhibits cell mitosis with EC50 of 9 nM and Cdc25C-T96 phosphorylation, a direct readout of PLK1 inhibition, with EC50 of 29 nM (Duffey, *Med Chem*, 55(1), 197-208 (2012)). The structure of MLN0905 is

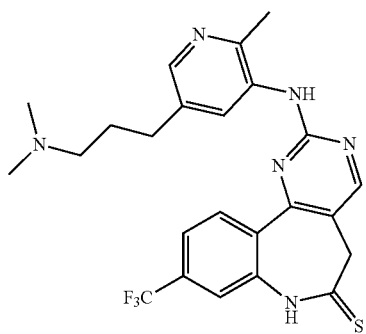 [SMILES: Cc1ncc(CCCN(C)C)cc1Nc1ncc2c(n1)-c1ccc(C(F)(F)F)cc1NC(=S)C2]

In preclinical experiments indicate an effective dosage range of about 1 mg/kg-50 mg/kg. One study indicates a preferred dosage of about 3-15 mg/kg with a maximum tolerated dose on QD (daily) schedule to be 6.25 mg/kg and on the QD×3/wk (3-days on/4-days off) schedule to be 14.5 mg/kg (Shi, et al., *Mol. Cancer Thera.*, 11(9), 2045-2053 (2012)).

RO$_{3280}$

RO$_{3280}$ is a potent, highly selective inhibitor of Polo-like kinase 1 (PLK1) with 1050 of 3 nM. The structure of RO$_{3280}$ is

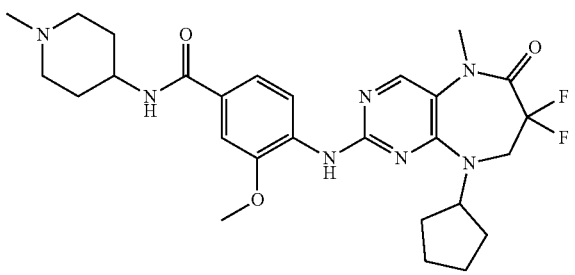 [SMILES: COc1cc(C(=O)NC2CCN(C)CC2)ccc1Nc1ncc2c(n1)N(C1CCCC1)CC(F)(F)C(=O)N2C]

RO$_{3280}$ shows the strong anti-proliferative activity against lung cancer cell line H82, colorectal cancer cell HT-29, breast cancer cell MDA-MB-468, prostate cancer cell PC3 and skin cancer cell A375 with IC50s of 5, 10, 19, 12 and 70 nM, respectively. RO$_{3280}$ also showed promising antitumor activity in nude mouse implanted with HT-29 human colorectal tumors ranging from 72% tumor growth inhibition when dosed once weekly at 40 mg/kg, to complete tumor regression when dosed more frequently (Chen, et al., *Bioorg. Med. Chem. Lett.*, 22(2), 1247-1250 (2012).

NMS-1286937

NMS 1286937, also known as NMS-P937, is an orally bioavailable, small-molecule Polo-like kinase 1 (PLK1) inhibitor with potential antineoplastic activity. Preclinical evaluation has shown high potency of the compound in proliferation assays, displaying low nanomolar activity on a large number of cell lines, representative of both solid and hematological tumors. A phase 1 dose escalation study of nms-1286937 administered to adult patients with advanced/metastatic solid tumors has been completed (Hartsink-Segers, et al., Haematologica. 98(10):1539-46 (2013)).

TAK-960

TAK-960 is an orally bioavailable, potent, and selective PLK 1 inhibitor that has shown activity in several tumor cell lines, including those that express multidrug-resistant protein 1 (MDR1) (Hikichi, et al., Mol Cancer Ther. 11(3): 700-9 (2012)). A Phase 1, open-label, dose-escalation study of orally administered TAK-960 has been completed.

CFI-400945 Fumarate

CFI-400945 is an inhibitor of polo-like kinase 4 (PLK4). Many tumors are shown to make too much PLK4. Phase 1 clinical trials of CFI-400945 fumarate delivered orally, at dose levels of 3, 6, 11, 16, 24, and 32 mg/day are currently underway (Mason, et al., *Cancer Cell*, V 26(2), pp. 163-176 (2014)).

b. Functional Nucleic Acid Inhibitors of PLK

In some embodiments, the polo-like kinase inhibitor is a functional nucleic acid that targets Plk1, Plk2/Snk, Plk3/Prk/FnK, Plk4/Sak, or Plk5. The functional nucleic acid can be, for example, an antisense molecule, aptamer, ribozyme, triplex forming oligonucleotide, external guide sequence, or RNAi that targets inhibits or reduces expression or translation of Plk1, Plk2/Snk, Plk3/Prk/FnK, Plk4/Sak, or Plk5 mRNA.

TKM-080301

In a particular embodiment, the Functional Nucleic Acid Inhibitor of PLK is TKM-080301. TKM-080301 has been effective when given in a 30-minute intravenous infusion. Phase clinical trials are currently underway, including doses ranging from 0.15 mg/kg per week to 0.9 mg/kg per week. Dose-limiting toxicities were observed at the 0.9 mg/kg per-week.

3. Additional Active Agents

In some embodiments, the combination therapy includes additional active agents. In addition to one or more antiandrogen or androgen antagonist, and one or more Plk inhibitors, the combination therapies can include any of the additional agents or components discussed herein, or known in the art to be coadministered with an antiandrogen or androgen antagonist, or with a Plk inhibitor. For example, abiraterone acetate is routinely administered in combination with a steroid such as prednisone or prednisolone. Therefore, in some embodiments, the combination includes prednisone or prednisolone.

In some embodiments, the combination therapy includes administration of an additional antiandrogen therapeutic agent, an immunotherapeutic agent, an agent for treating bone complications, a chemotherapeutic agent, or a combination thereof. In some embodiments, the combination therapy includes administration of an additional first or second line therapeutic agent for treatment of CRPC, such as one or more of the agents reviewed in Shapiro and Tareen, *Expert Rev. Anticancer Ther.*, 12(7):951-964 (2012), Heidegger, et al., *J. Steroid Biochem. Mol. Biol.*, 138(100): 248-256 (2013), and Lui, et al., *Cancer Control*, 20(3):181-187 (2013), each of which is specifically incorporated by reference herein in its entirety.

In some embodiments, the additional active agent is administered to the subject during the same cycle as the antiandrogen or androgen antagonist and Plk inhibitor. For example, the combination therapy can include a Plk inhibitor, abiraterone and a second antiandrogen or androgen antagonist. In a particular embodiment, the second antiandrogen or androgen antagonist is enzalutamide which is an androgen receptor inhibitor (Efstathiou, et al., *European Cancer Congress* 2013, Sep. 27-1, 2013, Amsterdam, The Netherlands, Abstract 2854).

It is appreciated that some combinations should not be administered simultaneously. Such combinations are preferably administered in series, for example using cycles, or drug holidays. For example, sipuleucel-T sold under the trade name PROVENGE® is an immune therapy that stimulates that immune system to attack the cancer. It is typically not advised to simultaneously administer abiraterone acetate and sipuleucel-T because abiraterone is typically administered simultaneously with a steroid. However, sequential administration of sipuleucel-T and abiraterone acetate has been proposed.

B. Formulations

Formulations of and pharmaceutical compositions including one or more active agents are provided. The combination therapies can include administration of the active agents together in the same admixture, or in separate admixtures. Therefore, the pharmaceutical compositions can include an antiandrogen or androgen antagonist, Plk inhibitor, or a combination thereof. In some embodiments, the pharmaceutical compositions can include one or more additional active agents. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of an antiandrogen or androgen antagonist, a Plk inhibitor, or a combination thereof. Effective amounts of the disclosed active agents are discussed in more detail below. It will be appreciated that in some embodiments the effective amount of antiandrogen or androgen antagonist, or Plk inhibitor in a combination therapy is different from that amount that would be effective for the antiandrogen or androgen antagonist, or Plk inhibitor to achieve the same result individually. For example, in some embodiments the effective amount of antiandrogen or androgen antagonist, or Plk inhibitor, is a lower dosage of the antiandrogen or androgen antagonist, or Plk inhibitor in a combination therapy than the dosage of the antiandrogen or androgen antagonist, or Plk inhibitor that is effective when one agent is administered without the other. Alternatively, in some embodiments the effective amount of antiandrogen or androgen antagonist, or Plk inhibitor, is a higher dosage of the antiandrogen or androgen antagonist, or Plk inhibitor in a combination therapy than the dosage of the antiandrogen or androgen antagonist, or Plk inhibitor that is effective when one agent is administered without the other. In other embodiments, the dosage of one agent is higher and the dosage of the other agent is lower than one agent is administered without the other. In some case, the agents are not effective when administered alone, and only effective when administered in combination.

1. Delivery Vehicles

The active agents can be administered and taken up into the cells of a subject with or without the aid of a delivery vehicle. Appropriate delivery vehicles for the disclosed active agents are known in the art and can be selected to suit the particular inhibitor. For example, in some embodiments, the active agent(s) is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

The active agent(s) can be incorporated into a delivery vehicle prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

Pharmaceutical compositions including active agent(s) with or without a delivery vehicle are provided. Pharmaceutical compositions can be for administration by parenteral (intramuscular, intraperitoneal, intravenous (IV) or subcutaneous injection), enteral, or transmucosal (nasal, vaginal, rectal, or sublingual) routes of administration or using bioerodible inserts and can be formulated in dosage forms appropriate for each route of administration.

In certain embodiments, the compositions are administered locally, for example, by injection directly into a site to be treated (e.g., into a tumor). In some embodiments, the compositions are injected or otherwise administered directly into the vasculature onto vascular tissue at or adjacent to the intended site of treatment (e.g., adjacent to a tumor). Typically, local administration causes an increased localized concentration of the compositions which is greater than that which can be achieved by systemic administration. Targeting of the molecules or formulation can be used to achieve more selective delivery.

a. Formulations for Parenteral Administration

Active agent(s) and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form including single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Kinase inhibitor and compositions thereof can be applied formulated for pulmonary or mucosal administration. The administration can include delivery of the composition to the lungs, nasal, oral (sublingual, buccal), vaginal, or rectal mucosa.

In one embodiment, the compounds are formulated for pulmonary delivery, such as intranasal administration or oral inhalation. The respiratory tract is the structure involved in the exchange of gases between the atmosphere and the blood stream. Pulmonary administration of therapeutic compositions including low molecular weight drugs has been observed, for example, beta-androgenic antagonists to treat asthma. Other therapeutic agents that are active in the lungs have been administered systemically and targeted via pulmonary absorption. The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e., non-aqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PART LC Jet+ nebulizer (PARS Respiratory Equipment, Monterey, Calif.).

Dry powder formulations ("DP's") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

C. Adjunct and Additional Therapies and Procedures

The combination therapies can be administered to a subject in combination with one or more adjunct therapies or procedures, or can be an adjunct therapy to one or more primary therapies or producers. The additional therapy or procedure can be simultaneous or sequential with the combination therapy. In some embodiment the additional therapy is performed between drug cycles or during a drug holiday that is part of the combination therapy dosage regime. In preferred embodiment, the additional therapy is a conventional treatment for cancer, more preferably a conventional treatment for prostate or breast cancer, most preferably a conventional treatment for hormone-resistant prostate or breast cancer. For example, in some embodiments, the additional therapy or procedure is surgery, a radiation therapy, or chemotherapy. For example, in a particular embodiment, combination therapies used simultaneously or sequentially with a regime of a chemotherapeutic agent, e.g., docetaxel or cabazitaxel. As discussed in more detail below, in some embodiment, the adjunct or additional therapy is part of the combination therapy.

III. Methods of Treatment

It has been established that androgen receptor antagonists or anti-androgens can be used in combination with inhibitors of Plk to provide enhanced antitumor activity as compared to the use of either agent alone. It is believed that inhibition of androgen receptor signaling by an androgen receptor antagonist or anti-androgen gives rise to an increased expression of genes involved in the retinoic acid receptor (RA) signaling pathway. Up-regulation of RA signaling is believed to enhance the sensitivity of cancer cells to Plk inhibitor activity. Further, the combined effects of RA up-regulation and Plk inhibitor activity are believed to inhibit or reduce the activity of the Nrf ½ (nuclear respiratory factor ½) and/or Elk1 transcription factors, and thereby reduce or inhibit the expression of genes that is driven by the Nrf1/2 or Elk transcription factors. Motifs bound by ELK1 and NRF1 positively correlate with malignant progression of breast cancer, colorectal tumors, Hepatoma and thyroid oncocytoma.

Methods of treating one or more symptoms of cancer in a subject are provided. In certain embodiments, the methods include administering to a subject with cancer an effective amount of an androgen receptor antagonist or anti-androgen, or a derivative, analog or prodrug, or a pharmacologically active salt thereof in combination with one or more inhibitors of Plk to reduce or inhibit one or more symptoms of the cancer. In preferred embodiments, the androgen receptor antagonist or anti-androgen and inhibitors of Plk can be used in combination to provide enhanced antitumor activity as compared to the use of either agent alone. The methods can include contacting one or more cancer cells expressing the androgen receptor and polo-like kinase with an effective amount of an androgen receptor antagonist or anti-androgen in combination with one or more inhibitors of Plk to decrease or inhibit the proliferation and/or viability of the cancer cells compared to untreated control cancer cells. In certain embodiments the methods are more effective in treating cancer in a subject having cancer cells that exhibit expression of one or more genes involved in the retinoic acid signaling pathway. In preferred embodiments, the cancer cells exhibit increased retinoic acid signaling relative to non-cancer cells. The genes involved in retinoic acid signaling can include Retinoic Acid Receptor Alpha (RARA); Retinoic Acid Receptor Gamma (RARG); Retinol Dehydrogenase (ADH4); and Retinaldehyde Reductase (DHRS3). In other embodiments, the methods are more effective in treating cancer in a subject having cancer cells that exhibit increased expression of one or more genes that contain binding sites for the transcription factors Nrf1/2 and/or Elk1 adjacent to their transcription start sites in response to combination treatment with an anti-androgen or androgen antagonist plus a Plk inhibitor.

The antiandrogen or androgen antagonist and Plk inhibitor can be administered locally or systemically to the subject, or coated or incorporated onto, or into a device.

A. Methods For Selecting Patients For Androgen Antagonist and Plk Inhibitor Combination Therapies Methods for characterizing tumors and/or for characterizing the tumor microenvironment are provided. In particular, the disclosure pertains to methods for characterizing tumors so as to assess the extent to which the tumor cells and/or tumor infiltrating cells or tumor associated cells express genes associated with sensitivity to combination therapy with androgen receptor antagonist or anti-androgen, in combination with one or more inhibitors of Plk. For example, tumor cells and/or tumor infiltrating cells or tumor associated cells that are sensitive to more than additive effects of combination therapy with androgen receptor antagonist or anti-androgen in combination with one or more inhibitors of Plk can express genes involved in the Retinoic Acid Receptor (RA) signaling pathway prior to treatment, and/or show up-regulation of genes driven by the NRF½ or Elk1 transcription factors after combination treatment. The disclosure concerns the uses of such methods in the diagnosis and the treatment of cancer and other diseases. Therefore, methods for characterizing a cell of a tumor are provided. The methods can include determining whether a cell of the tumor expresses one or more of the components of the Retinoic Acid Receptor (RA) signaling pathway, specifically genes involved in retinoic acid signaling, including Retinoic Acid Receptor Alpha (RARA); Retinoic Acid Receptor Gamma (RARG); Retinal Dehydrogenase (ADH4); and Retinaldehyde Reductase (DHRS3).

Methods for assessing the amenability of subject to a proposed anti-cancer therapy are also provided. The methods can include, for example, characterizing cells of a tumor of the subject by determining whether the cells of the tumor express genes that are associated with sensitivity to more than additive effects of androgen receptor antagonist or anti-androgen in combination with one or more inhibitors of Plk. For example, subjects having cancer cells that express genes involved in the Retinoic Acid Receptor (RA) signaling pathway can be selected for treatment with an androgen receptor antagonist or anti-androgen in combination with one or more inhibitors of Plk. Methods for assessing the efficacy of an anti-cancer therapy provided to a subject are also disclosed. The methods can include, for example, characterizing cells of a tumor of the patient during the course of the therapy or after the completion thereof, wherein said characterization can include determining whether the cells of the tumor express genes involved in the Retinoic Acid Receptor (RA) signaling pathway, or show increased expression of genes that are driven by the Nrf1/2 or Elk1 transcription factors in response to the treatment.

Methods for selecting patients for anti-cancer therapy based on characterization of the tumor or tumor microenvironment are also provided. In some embodiments, cancer patient tumor samples are characterized prior to and following treatment with following specific chemotherapeutic and/or biologic therapies, and/or other therapeutic interventions (e.g. radiation, cryoablation, surgical resection of the tumor, etc.) in order to see if the expression patterns of genes involved in the Retinoic Acid Receptor (RA) signaling pathway, or genes that are driven by the Nrf1/2 or Elk1 transcription factors, within the tumor microenvironment have changed.

The methods typically include detecting genes involved in the Retinoic Acid Receptor (RA) signaling pathway, or genes that are driven by the Nrf1/2 or Elk1 transcription factors, alone or in combination with one or more other biomarkers of cancer cells. Suitable methods of detection are known in the art. For example, some of the disclosed methods include a step of contacting the cell of the tumor with a molecule that immunospecifically or physiospecifically binds proteins involved in the Retinoic Acid Receptor (RA) signaling pathway, or examining RNA expression for genes regulated by the Nrf½ or Elk1 transcription factors using VCR, microarray methods, or RNA-Seq. In some preferred embodiments, the molecule that immunospecifically or physiospecifically binds proteins involved in the Retinoic Acid Receptor (RA) signaling pathway is an antibody or an antigen-binding fragment thereof.

B. Methods of Administration and Dosage Regimes

The combination therapies and treatment regimens typically include treatment of a disease or symptom thereof, or a method for achieving a desired physiological change, including administering to an animal, such as a mammal, especially a human being, an effective amount of an anti-androgen or androgen antagonist and a Plk inhibitor to treat the disease or symptom thereof, or to produce the physiological change, wherein the chemical agents or components are administered together, such as part of the same composition, or administered separately and independently at the same time or at different times (i.e., administration of the antiandrogen or androgen antagonist and the Plk inhibitor is separated by a finite period of time from each other). Therefore, the term "combination" or "combined" is used to refer to either concomitant, simultaneous, or sequential administration of the antiandrogen or androgen antagonist and the Plk inhibitor. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

When used for treating cancer, the amount of antiandrogen or androgen antagonist present in a pharmaceutical dosage unit, or otherwise administered to a subject can be the amount effective to reduce the proliferation, viability, or a combination thereof of the cancer cells when administered in combination with a Plk inhibitor. Likewise, the amount of Plk inhibitor present in a pharmaceutical dosage unit, or otherwise administered to a subject can be the amount effective to reduce the proliferation, viability, or a combination thereof of the cancer cells when administered in combination with an antiandrogen or androgen antagonist. Therefore, in some embodiments the amount of the active agents is effective to reduce, slow or halt tumor progression, to reduce tumor burden, or a combination thereof. In some embodiment, the amount of the active agents is effective to alter a measureable biochemical or physiological marker. For example, if the cancer is prostate cancer, the amount of the active agents can be effective to reduce the level of prostate specific antigen (PSA) concentration in the blood compared to the PSA concentration prior to treatment. In some embodiments, the active agents are administered in an effective amount to reduce or prevent cancer progression despite a rise in androgen levels or PSA concentration in levels.

In preferred embodiments, administration of the antiandrogen or androgen antagonist and the Plk inhibitor achieves a result greater than when the antiandrogen or androgen antagonist and the Plk inhibitor are administered alone or in isolation. For example, in some embodiments, the result achieved by the combination is partially or completely additive of the results achieved by the individual components alone. In the most preferred embodiments, the result achieved by the combination is more than additive of the results achieved by the individual components alone. In some embodiments, the effective amount of one or both agents used in combination is lower than the effective amount of each agent when administered separately. In some embodiments, the amount of one or both agents when used in the combination therapy is sub-therapeutic when used alone.

The effect of the combination therapy, or individual agents thereof can depend on the disease or condition to be treated or progression thereof. For example, as illustrated in the Examples below, an agent such is abiraterone can be used a first or second line therapy for treatment of prostate cancer. However, over time, the cancer can develop a resistance to abiraterone. Subsequent treatment of the cancer with abiraterone in combination with a Plk inhibitor such as BI2536 "re-sensitizes" the cancer to abiraterone treatment. Accordingly, in some embodiments, the effect of the combination on a cancer can compared to the effect of the individual agents alone on the cancer.

The Examples illustrate that the effect of the combination therapies can be hormone independent (e.g., is still effective in the presence of rising levels of androgens). Therefore, in some embodiments, the combination therapy performs similarly to the individual components when used alone, but remains effective in presence of rising hormone levels. Accordingly, the combination is improved over the individual components alone. Although the cancer killing effect of the combination is similar to the individual components, the duration of efficacy of the treatment is longer because the cancer does not become resistant to the treatment. This allows the combination therapies to be administered in combination with or as an alternative to hormone therapy, a first line therapy, or a second line or subsequent therapy, and without the need of the cancer to first become resistant to the antiandrogen or androgen antagonist (e.g., abiraterone).

A treatment regimen of the combination therapy can include one or multiple administrations of antiandrogen or androgen antagonist. A treatment regimen of the combination therapy can include one or multiple administrations of Plk inhibitor. In certain embodiments, an antiandrogen or androgen antagonist can be administered simultaneously with a Plk inhibitor. Where an antiandrogen or androgen antagonist and a Plk inhibitor are administered at the same time, the antiandrogen or androgen antagonist and the Plk inhibitor can be in the same pharmaceutical composition.

In some embodiments an antiandrogen or androgen antagonist and a Plk inhibitor are administered sequentially, for example, in two or more different pharmaceutical compositions. In certain embodiments, the antiandrogen or androgen antagonist is administered prior to the first administration of the Plk inhibitor. In other embodiments, the Plk inhibitor is administered prior to the first administration of the antiandrogen or androgen antagonist. For example, the antiandrogen or androgen antagonist and the Plk inhibitor can be administered to a subject on the same day. Alternatively, the antiandrogen or androgen antagonist and the Plk inhibitor are administered to the subject on different days.

The Plk inhibitor can be administered at least 1, 2, 3, 5, 10, 15, 20, 24 or 30 hours or days prior to or after administering of the antiandrogen or androgen antagonist. Alternatively, the Plk inhibitor can be administered at least 1, 2, 3, 5, 10, 15, 20, 24 or 30 hours or days prior to or after administering of the Plk inhibitor. In certain embodiments, additive or more than additive effects of the administration of antiandrogen or androgen antagonist in combination with one or more Plk inhibitors is evident after one day, two days, three days, four days, five days, six days, one week, or more than one week following administration.

Dosage regimens or cycles of the agents can be completely or partially overlapping, or can be sequential. For example, in some embodiments, all such administration(s) of the antiandrogen or androgen antagonist occur before or after administration of the Plk inhibitor. Alternatively, administration of one or more doses of the antiandrogen or androgen antagonist can be temporally staggered with the administration of Plk inhibitor to form a uniform or non uniform course of treatment whereby one or more doses of antiandrogen or androgen antagonist are administered, followed by one or more doses of Plk inhibitor, followed by one or more doses of antiandrogen or androgen antagonist; or one or more doses of Plk inhibitor are administered, followed by one or more doses of antiandrogen or androgen antagonist, followed by one or more doses of Plk inhibitor; etc., all according to whatever schedule is selected or desired by the researcher or clinician administering the therapy.

An effective amount of each of the agents can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days, are all specifically contemplated.

C. Diseases to be Treated

The combination therapies are typically used to treat cancer, preferably a hormone-sensitive or hormone-dependent cancer that has become hormone-insensitive. Typically, hormone-sensitive cancers are initially dependent on a hormone for cancer growth. Altering the cancer's hormone supply through hormone therapy such as radiation therapy, drugs that alter hormone production, anti-hormones, aromatase inhibitors, Luteinizing hormone-releasing hormone (LH-RH) agonists and antagonists, or surgery to remove hormone producing tissue or organs, can make the tumors shrink and even lead to cancer remission. However, the effects of hormone therapy can be limited. Hormone sensitive cancers often become hormone-insensitive, meaning the cancer is no longer responsive to hormone therapy, although in most cases the tumor is still driven by intracellular hormonal signaling. The combination therapies are particularly effective for treating hormone-sensitive cancers that have become hormone-insensitive. Exemplary cancers include, but are not limited to, prostate cancer, breast cancer, ovarian cancer, and endometrial cancer.

When hormone therapy is no longer effective, subjects with hormone-insensitive cancers are typically administered a first line therapy. However, in many cases, the cancer cells also develop resistance to the first line therapy. For some hormone-insensitive cancers there are second line therapies available, however, over time the cancer cells can also develop resistance to the second line therapy. As discussed in more detail below, the combination therapies can re-sensitize cancer cells to a first or second-line therapy. Therefore, in some embodiments, the combination therapies are used to treat subjects with a hormone-insensitive cancer that is also resistant to a first line therapy, a second line therapy, or a combination thereof. In some cases the first line therapy, second line therapy, or a combination thereof includes the administration of one of the active agents of the combination therapy without co-administration of the other active agent. Therefore, in some embodiments administration of the combination therapy re-sensitizes the cancer cells to an active agent that was previously administered to the subject as a first or a second line therapy. In preferred embodiments, the re-sensitization is effective even in the presence of rising hormone levels.

In preferred embodiments, the cancer cells can express the androgen receptor, and/or the cancer is an androgen-sensitive cancer that has become androgen-insensitive (also referred to as an androgen-independent cancer). Androgen-independent cancer is typically a cancer that has reacquired an ability to grow following temporary suppression of the cancer's ability to grow by inhibiting androgen production or function. In some embodiments, suppression of the cancer's ability to grow refers to suppression of tumor growth or another symptom of the cancer, for example, amelioration of ostealgia.

Suppression of the cancer's ability to grow using a hormone therapy or physical castration (e.g., orchiectomy), can be measured using a biochemical assay, for example, measuring a decline in the prostate specific antigen (PSA) concentration in the blood, or by a morphometric analysis, for example by computerized tomography (CT), magnetic resonance imaging (MRI) or ultrasound. A decline in the blood PSA concentration effective to reduce an androgen sensitive cancer's ability to grow is typically a blood PSA concentration of about or below 5 ng/mL, about or below 1 ng/ml, about or below 0.5 ng/ml, about or below 0.2 ng/ml, about or below 0.1 ng/ml, or undetectable.

A cancer that has reacquired an ability to grow can be an increase in tumor growth, the emergence, reemergence, or aggravation of other symptoms such as ostealgia, new sites of metastasis, or a rise in blood PSA. A sustained rise in blood PSA concentration observed in the course of periodic tests can indicate that the cancer has reacquired the ability to grow. A blood PSA concentration of, for example, about 5 ng/mL or more can also indicate that the cancer has reacquired the ability to grow. Because various factors (such as sexual activity) can cause PSA levels to fluctuate, one abnormal PSA test does not necessarily indicate a problem.

In other embodiments, the cancer does not express or over express AR or ER.

1. Prostate Cancer

The cancer can be prostate cancer. Prostate cancer is the most frequently diagnosed malignancy in men in Western countries. While localized prostate cancer can be effectively treated with surgery or radiation therapy, metastatic PCa still remains incurable. For locally advanced or widespread disease, suppressing the tumor growth by hormone ablation therapy represents the common first therapeutic option (Beltran, et al., *European Urology*, 60:279-290 (2011)). Although initial therapy can lead to long-term remission, development of hormone ablation resistance can eventually occur, a standing referred to as castration-resistant prostate cancer (CRPC). Therefore, in some embodiments, the subject has a CRPC. Unlike early prostate cancer, CRPC is an aggressive disease that progresses despite castrate levels of testosterone ($\leq 50$ ng/ml). It is diagnosed by one or more of the following discussed above for androgen-insensitive cancers (e.g., sustained rise in serum levels of prostate-specific antigen (PSA), progression of pre-existing disease, the appearance of new metastases, or a combination thereof).

Subjects with CRPC are typically administered a first line therapy. Docetaxel and sipuleucel-T are exemplary first line treatment options for patients with CRPC. Second-line treatments following first line treatment failure include cabazitaxel and abiraterone acetate. The history of first and second line therapeutic options for subjects with CRPC are reviewed in Shapiro and Tareen, *Expert Rev. Anticancer Ther.*, 12(7):951-964 (2012) and Heidegger, et al., *J. Steroid Biochem. Mol. Biol.*, 138(100): 248-256 (2013), which are both specifically incorporated by reference herein in their entireties. The combination therapies can be administered to subjects which have previously been administered a first line therapy for CRPC and/or a second line therapy for CRPC. In a particular embodiment, the combination therapy is administered to subject when a first line therapy and/or a second line therapy have become ineffective to treat or prevent progression of the cancer.

In a particular embodiment, the combination therapy is administered to a subject that was previously administered an agent that targets and inhibits androgen receptor activity. The agent can target androgen receptor activity directly, or indirectly, for example by inhibiting androgen synthesis. In a particular preferred embodiment, the subject was previously administered an abiraterone-based therapy such as ZYTIGA® (abiraterone acetate). Abiraterone has been administered to subjects as a first line therapy and as a second line therapy, typically following chemotherapy, for treatment of CRPC. The data presented in the working Examples below illustrates that the combination therapies are effective to treat cancers that have become resistant to abiraterone.

2. Breast Cancer

The cancer can be breast cancer, preferably a breast cancer characterized by breast cancer cells that expresses the androgen receptor. Androgens play a role in normal breast physiology and androgen receptor (AR) signaling is recognized as an important contributor in breast carcinogenesis (Garay, et al., *Am. J Cancer Res.*, 2(4):434-445 (2012)). The androgen receptor is expressed in most breast cancers, and although the mechanism underlying the androgen receptor's role in cancer progression remains unclear, it has been identified as a potential therapeutic target for breast cancer treatment. Therefore, in some embodiments, the combination therapy is administered to treat a breast cancer, preferably, but not limited to, an androgen receptor-positive breast cancer.

The success of estrogen receptor/progesterone receptor (ER/PR) and HER2 targeted therapies has shifted interest in androgen receptor to those breast cancers that lack ER/PR and/or HER2 expression, often referred to as "triple negative breast cancer" or "triple negative disease". In addition, AR targeted therapies may also be important for breast cancers that have developed resistance to current hormone and HER2 directed therapies. Therefore, in some embodiments, the breast cancer lacks ER, PR, or HER2 expression, or a combination thereof (e.g., triple negative disease), is a hormone-insensitive cancer, is resistant to a HER2 directed therapy, or any combination thereof.

It has also been shown both in vitro and in vivo that combinatorial therapy targeting both the MAP kinase pathway and AR is an effective means of reducing tumor cell viability and tumor burden (Naderi and Liu, *Cancer Lett.*, 298: 74-87 (2010)). Therefore, in some embodiments, the combination therapies include an inhibitor of the MAP kinase pathway.

3. Other Cancers

The compositions and methods described can be used to treat multiple types of cancer. It has been established that an androgen receptor antagonist or anti-androgen, or a derivative, analog or prodrug, or a pharmacologically active salt thereof in combination with one or more inhibitors of Plk can give rise to profound greater than additive killing of cancers that are not associated with consistent expression of Androgen receptor signaling or other steroid hormone or growth factors. Therefore, multiple non-hormonal cancers can be treated using the compositions and methods described herein.

The combination is particularly effective in treating cancers characterized by up-regulated expression of genes that are involved in the Retinoic Acid Receptor (RA) signaling pathway, specifically genes including the Retinoic Acid Receptor Alpha (RARA); Retinoic Acid Receptor Gamma (RARG); Retinol Dehydrogenase (ADH4); and Retinaldehyde Reductase (DHRS3). Cancers that have been identified as having up-regulated expression of genes that are involved in the Retinoic Acid Receptor (RA) signaling pathway include multiple types of cancers, including but not limited to prostate, breast, and pancreatic cancers.

Pancreatic cancers include pancreatic adenocarcinoma or pancreatic exocrine cancer, and often have a poor prognosis, even when diagnosed early. Pancreatic cancer typically spreads rapidly and is seldom detected in its early stages, and pancreatic carcinoma is a leading cause of cancer death. Signs and symptoms can include upper abdominal pain; bowel obstruction; back pain; yellow discoloration of the skin and whites of the eye (i.e., jaundice); reduced appetite; weight loss; depression; and blood clots. Symptoms may not appear until pancreatic cancer is quite advanced and complete surgical removal is not possible.

Gene expression profiles for cancer cells within a tumor or for cells within the tumor micorenvironment can be determined in vitro or in vivo by any means known in the art. Genomic databases can also be used as a guide for the selection of pharmacologic vulnerabilities to genomic patterns. Such databases include the Cancer Cell Line Encyclopedia (CCLE), including gene expression profile information for human cancer cell lines (Stransky, et al. Nature 483, 603-307 (2012)).

A representative, but non-limiting, list of cancers that the disclosed compositions and methods can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, skin cancer, liver cancer, melanoma, squamous cell carcinomas of the mouth, throat, larynx, and lung, colon cancer, cervical cancer, cervical carcinoma, epithelial cancer, renal cancer, genitourinary cancer, pulmonary cancer, esophageal carcinoma, head and neck carcinoma, large bowel cancer, hematopoietic cancers; testicular cancer; colon and rectal cancers, and pancreatic cancer.

D. Compositions for Use in Disease Treatment

Compositions for use in the treatment of the disclosed diseases are also provided. For example, a composition including an antiandrogen or androgen antagonist for use in a method of treating a subject with cancer, wherein the subject is one whom a composition including a Plk inhibitor has previously been or is concurrently being administered and wherein the response achieved following the administration of antiandrogen or androgen antagonist is greater than the response achieved by administering either the antiandrogen or androgen antagonist alone or the Plk inhibitor alone are disclosed.

In another embodiment, a composition including a Plk inhibitor for use in a method of treating a subject with cancer, wherein the subject is one whom a composition including an antiandrogen or androgen antagonist has previously been or is currently being administered and wherein the response achieved following the administration of the Plk inhibitor is greater than the response achieved by administering either the antiandrogen or androgen antagonist alone or the Plk inhibitor alone is provide. Suitable compositions, cancers to be treated, dosage regimes, and responses achieved by administering the combinations are discussed at length above. In particular embodiments the subject may have been previously administered one or more of the drugs, but not in combination.

Furthermore, it will be appreciated as discussed above, that the cancer may have developed a resistance to the previously administered active agent the active agent is administered in the absence of the combination. Therefore, in some embodiments, the subject population being treatment is defined as one in which the cancer being treated is resistant or insensitive to one or the other of the active agent when administered alone.

IV. Kits

Medical kits are also disclosed. The medical kits can include, for example, a dosage supply of an antiandrogen or androgen antagonist, a polo-like kinase inhibitor, or a combination thereof in separately or together in the same admixture. The active agents can be supplied alone (e.g., lyophilized), or in a pharmaceutical composition. The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

EXAMPLES

Example 1: Prostate Cancer Cells are Sensitive to Plk1 Inhibition

Materials and Methods

Prostate cancer cell lines (LNCaP and C4-2) were seeded into 96-well plates in RPMI-1640 medium containing 10 fetal-bovine serum depleted of androgen by activated charcoal-dextran (csFBS). Twenty four hours later, the indicated concentration of BI2536 and R1881 were added, representing time zero. Viability of the prostate cancer cells was assessed using Cell-Titer Glo™ according to the manufacturer's instructions.

Results

Figure 3A:
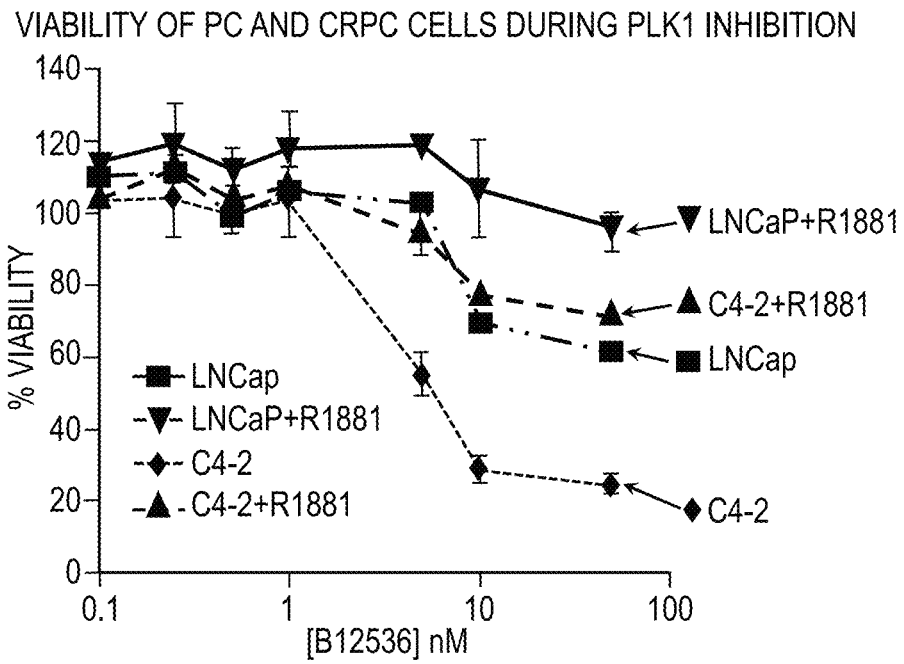
FIG. 3A is a line graph showing the % viability of prostate cancer (LNCaP—androgen-sensitive human prostate adenocarcinoma cells) and castrate resistant (CRPC) cells (C4-2) in the presence of increasing concentrations of Plk1 inhibitor (BI2436 nM), and in the presence or absence of synthetic androgen (R1881).

An experiment was designed to test the effect of Plk1 on prostate cancer cells. The androgen-sensitive cells (LNCaP) and castrate resistant prostate cancer cells (CRPC) (C4-2) were treated with increasing concentrations of BI2536 in the presence and absence of synthetic androgen (R1881). The results, shown in FIG. 3A shows that viability of both cell lines is reduced in the presence of BI2536, but the viability can be somewhat rescued in the presence of synthetic androgen.

Figure 3B:
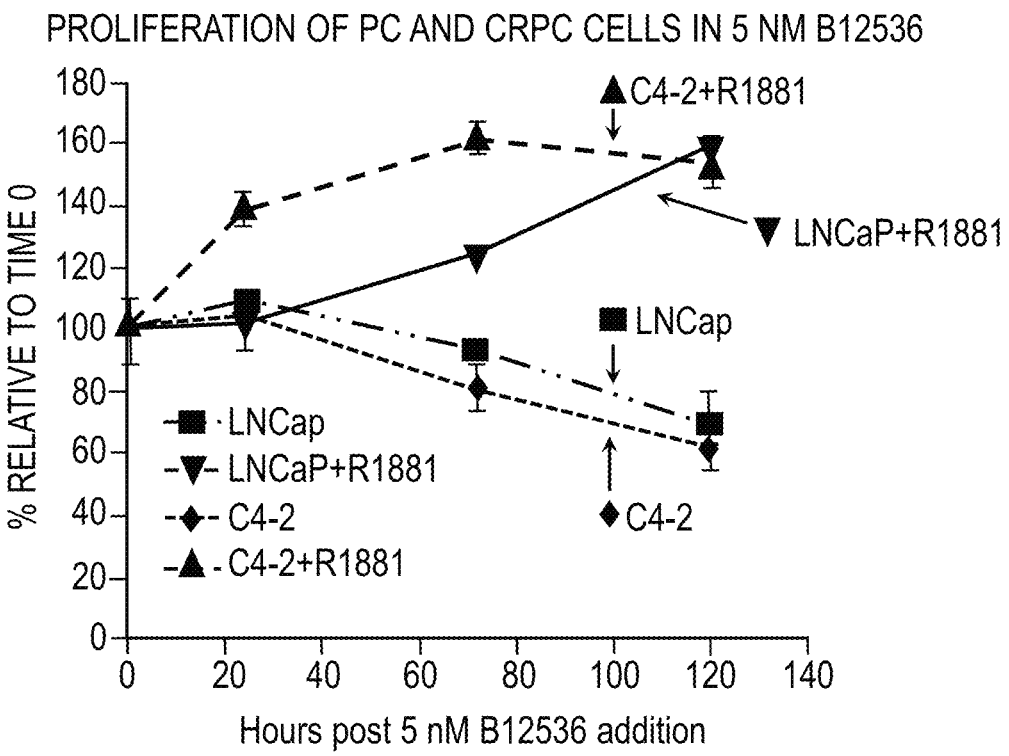
FIG. 3B is a line graph showing the proliferation (% relative to time 0) of prostate cancer cells (LNCaP-androgen-sensitive human prostate adenocarcinoma cells) and CRPC (C4-2) cells over time (hours) after administration of Plk1 inhibitor (BI2436 at 5 nM), and in the presence or absence of synthetic androgen (R1881).

FIG. 3B shows the results of an assay measuring the proliferation of cells over time in the presence of 5 nM BI2536. The results indicate that proliferation of both cell lines is reduced in the presence of BI2336, but proliferation can be somewhat rescued in the presence of synthetic androgen Thus increased androgen receptor activity can drive proliferation despite the loss of Plk1 activity.

Together, the results indicate that CRPC cells are particularly dependent on Plk1 activity when the AR is not sufficiently stimulated.

Example 2: The Effect of Co-Treatment with BI2536 and Abiraterone on Prostate Cancer Cells is More Than Additive Materials and Methods For FIG. 4, CRPC cells (C4-2) were seeded into 96-well plates in RPM-1640 medium containing 10% FBS (not stripped with charcoal-dextran). 24 hours later the indicated concentrations of Abiraterone and/or BI2536 were added, representing day 0. Viability was measured for the subsequent five days using Cell-Titer Glo™ according to the manufacturer's instructions.

Figure 5A:
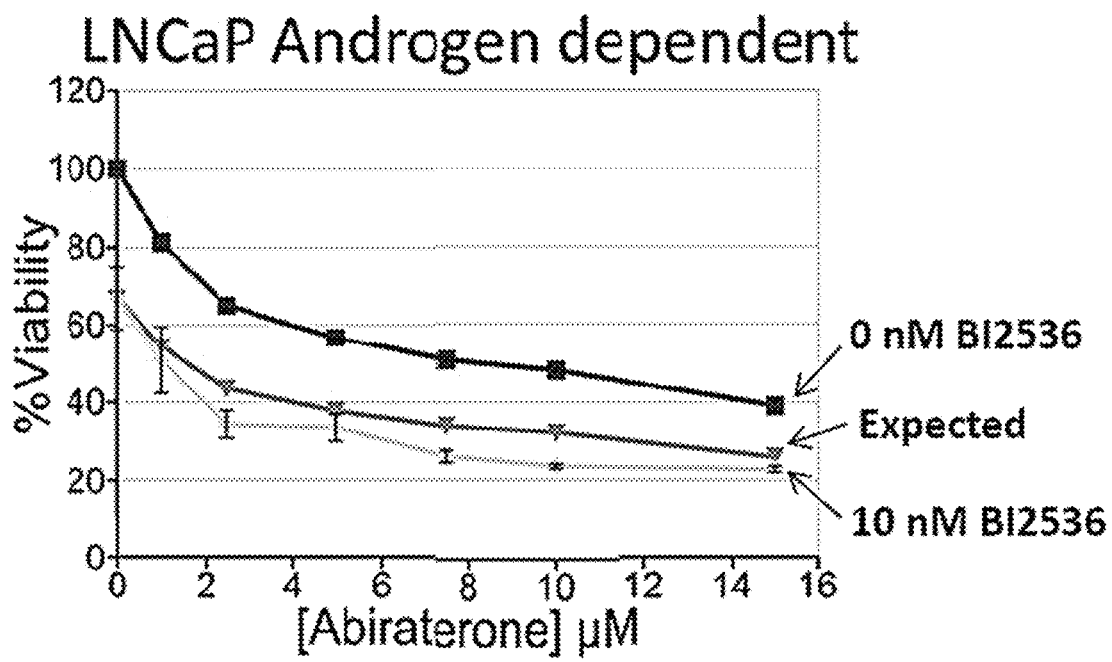
FIGS. 5A, 5B, and 5C are line graphs showing the % viability of prostate cancer cell lines LNCaP-androgen dependent cells (5A), 22 RV1-castrate resistant (5B), and C4-2-castrate resistant (5C) in the presence of increasing concentrations of abiraterone (µM), and in the presence (10 nm (-◆-)) or absence (0 nm (-■-)) of Plk inhibitor (BI2536). The predicted additive result of the two agents in combination is shown as "expected" (-▼-).
Figure 5B:
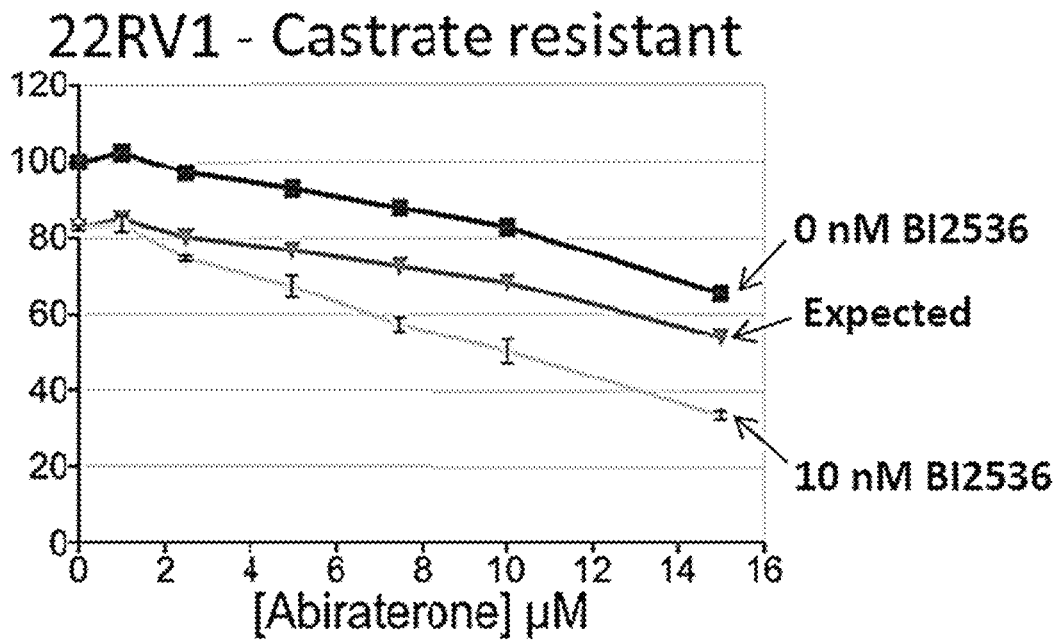
Figure 5C:
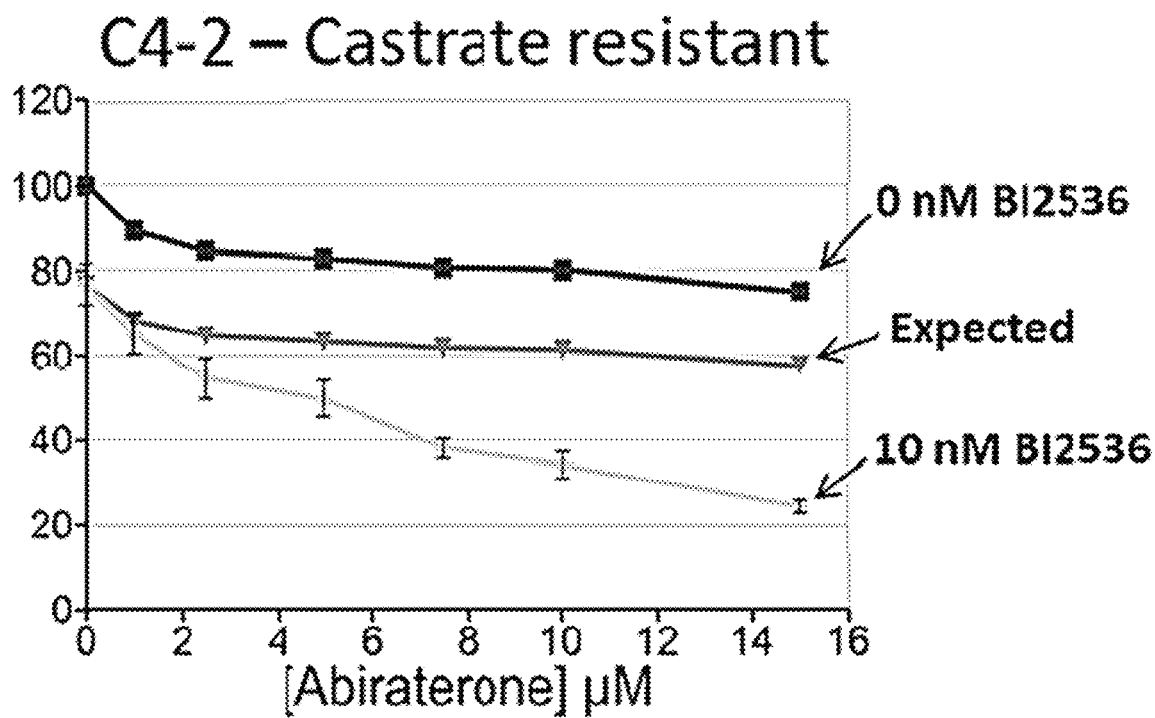

Dose response curves presented in FIG. 5A-C were measured by seeding into 96 well plates CRPC cells (C4-2 and 22 RV1) and androgen dependent prostate cancer cells (LNCaP) in RPM 1640 containing 10% csFBS or FBS, respectively. Twenty four hours later the indicated concentrations of Abiraterone and 5 nM BI2536 were added. Cell viability was assessed after 5 days using Cell-Titer Glo™ according to the manufacturer's instructions.

Results

Figure 4:
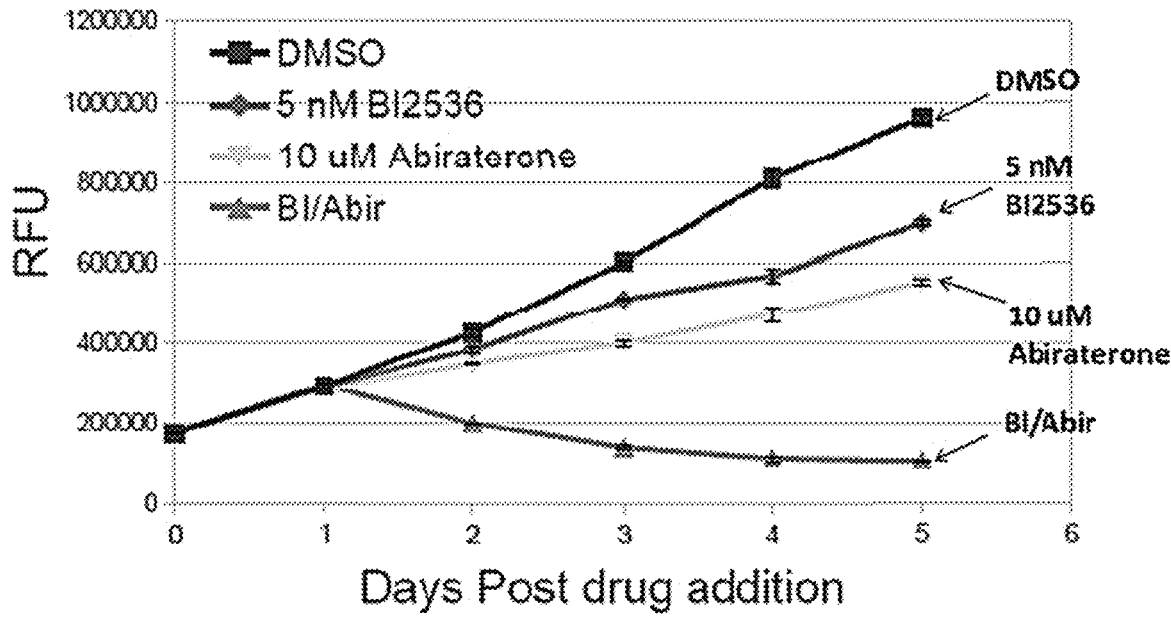
FIG. 4 is a line graph showing proliferation (RFU following Celltiter Glo assay) of CRPC (C4-2) cells treated with DMSO, 5 nM BI2536, 10 µM abiraterone, or 5 nM BI2536 and 10 µM abiraterone over time (days post drug administration).

Experiments were designed to test the effect of co-administration of BI2536 and abiraterone on the proliferation prostate cancer cells. CRPC cells (C4-2) were treated with vehicle (DMSO), 5 nM BI2536, 10 µM abiraterone, or 5 nM BI2536 in combination with 10 µM abiraterone and proliferation was monitored over 5 days post-administration. These experiments were done in medium containing FBS and physiological levels of androgen. The results, shown in FIG. 4 shows that relative levels of proliferation are reduced over time in the presence of 5 nM BI2536, alone, and 10 µM abiraterone alone, but synergistically reduced when the two agents are administered in combination. Moreover, the combination of abiraterone and BI2536 resulted in a decrease in cell viability over time, indicating a loss of cell number as opposed to a cytostatic effect.

FIGS. 5A-5C show the results of assays measuring the % viability of cells (LNCaP-androgen dependent; 22 RV1-castrate resistant; and C4-2-castrate resistant) after five days in the presence (-◆-) or absence (-■-) of 10 nM BI2536 and increasing concentrations of abiraterone. The expected viability if abiraterone and BI2536 were acting in an additive manner is also indicated (-▼-). The results indicate that, particularly with CRPC cells, the reduction in % viability of cells treated with both agents is reduced to a greater degree than predicted based an additive effect of the combination.

Together, the results indicate that the effect of the combination of BI2536 and abiraterone on prostate cancer cells, including castrate resistant prostate cancer cells is more than additive. While the CRPC cells are relatively resistant to Abiraterone in the absence of BI2536, their sensitivity is essentially equivalent to androgen dependent cells when a low concentration of Plk inhibitor is added. These results can lead to a conclusion that castrate resistant prostate cancer cells are sensitized to abiraterone by BI2536.

Example 3: The Effect of Co-Treatment with BI2536 and Abiraterone on Breast Cancer Cells is More than Additive Materials and Methods The breast cancer cell lines AU565 (expresses the AR) and BT20 (does not express the AR) were seeded into 96-well plates in DMEM medium containing 10% FBS. Twenty four hours later the indicated concentrations of Abiraterone and 5 nM BI2536 were added. Cell viability was assessed after 5 days using Cell-Titer Glo™ according to the manufacturer's instructions.

Results

Figure 6A:
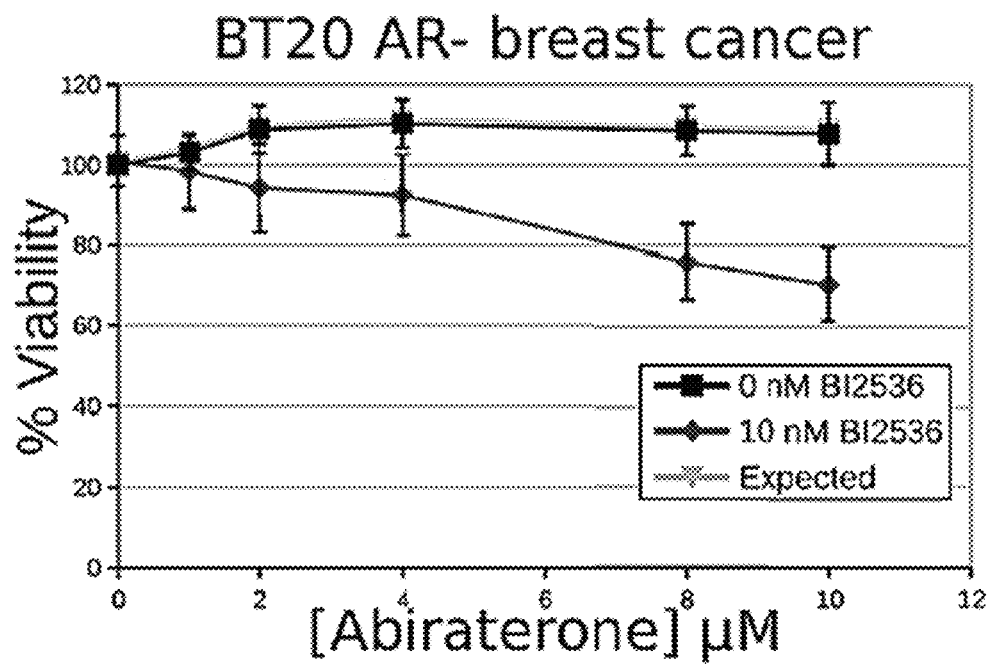
FIGS. 6A and 6B are line graphs showing the % viability of breast cancer cell lines BT20-AR-(6A) and AU565-AR+ (6B) in the presence of increasing concentrations of abiraterone (µM), and in the presence ((-◆-) or absence (-■-) of Plk inhibitor (BI2536). The concentration of BI2536 used was 2 nM or 10 nM for AU565 and BT20, respectively. The predicted additive result of the two agents in combination is shown as "expected" (-▼-).
Figure 6B:
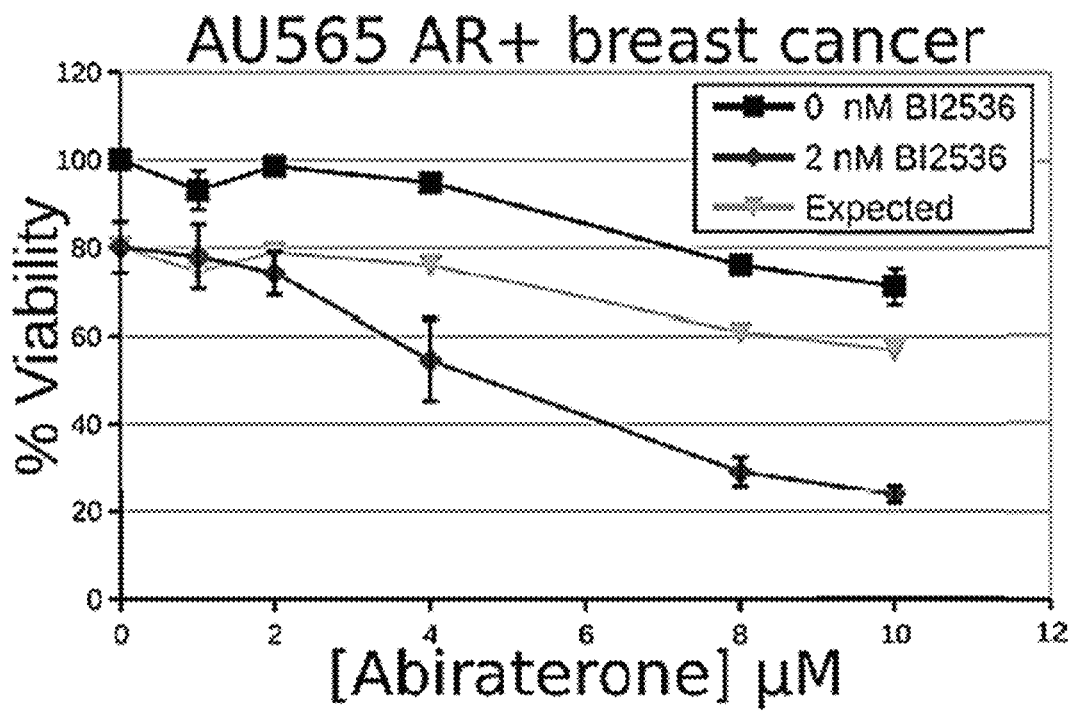

Experiments were designed to test the effect of co-administration of BI2536 and abiraterone on breast cancer cells. FIGS. 6A and 6B show the results of assays measuring the % viability of the AU565 and BT20 cells in the presence (-◆-) or absence (-■-) of BI2536 and increasing concentrations of abiraterone. The expected outcome if these agents were acting in an additive manner is also indicated (-▼-). The results indicate % viability of cells treated with both agents is reduced to a greater degree than predicted based an additive effect of the combination, Together, the results indicated that the effect of the combination of BI2536 and abiraterone on breast cancer cells is more than additive. These results can lead to a conclusion that some breast cancer cells are sensitized to abiraterone by BI2536. Moreover, because the nature of prostate cancer and breast cancer is substantially different, the observation that BI2536 synergizes with abiraterone in both cell types indicates that this is a fundamental characteristic of these signaling proteins and not a peculiarity of the relatively few CRPC cell lines available.

Example 4: The Effect of Co-Treatment with BI2536 and Abiraterone is Not a Result of G2/M Arrest Materials and Methods CRPC cells (C4-2 and 22 RV1) and androgen dependent prostate cancer cells (LNCaP) were seeded in 96-well plates using RPMI 1640 containing 10% csFBS or FBS, respectively. Twenty four hours later the indicated concentrations of Abiraterone and 5 nM Docetaxel were added. Cell viability was assessed after 4 days using Cell-Titer Glo™ according to the manufacturer's instructions.

Results

Experiments were designed to investigate the mechanism underlying the effect of co-administration of BI2536 and abiraterone. Previously reported experiments have indicated that BI2536 can induce cell cycle arrest.

Figure 7A:
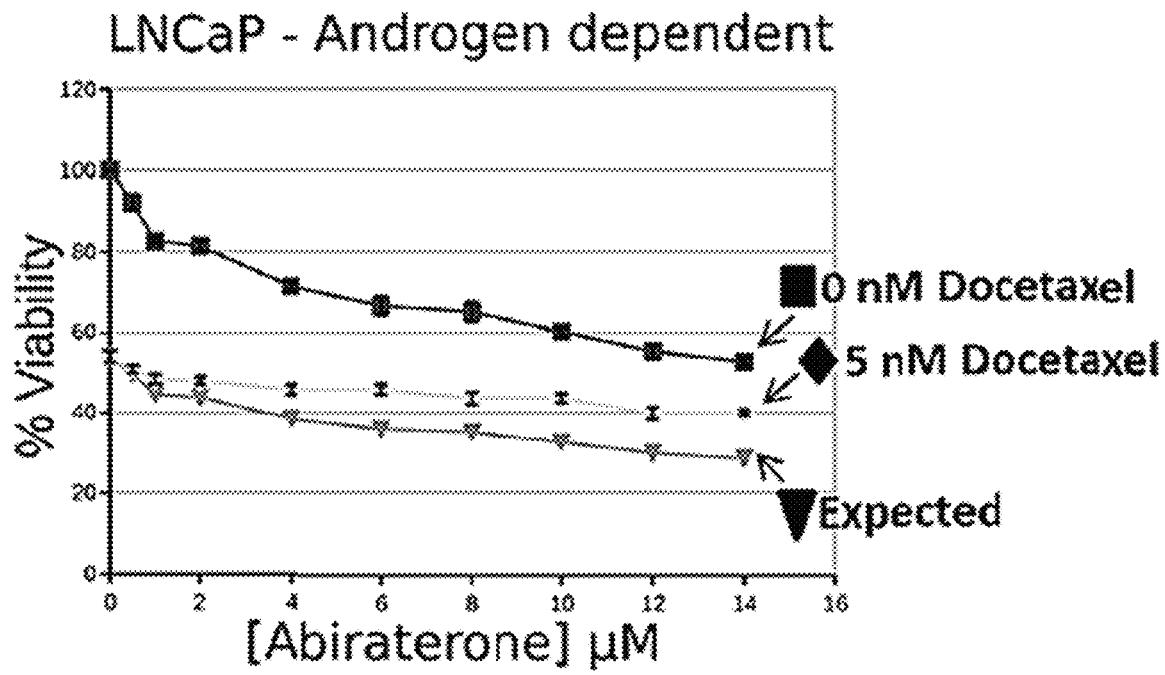
FIGS. 7A, 7B, and 7C are line graphs showing the % viability of prostate cancer cell lines LNCaP-androgen dependent cells in FBS (7A), 22 RV1-castrate resistant in csFBS (7B), and C4-2-castrate resistant in csFBS (7C) in the presence of increasing concentrations of abiraterone (µM), and in the presence (5 nm (-◆-)) or absence (0 nm (-■-)) of docetaxel. The predicted additive result of the two agents in combination is shown as "expected" (-▼-).
Figure 7B:
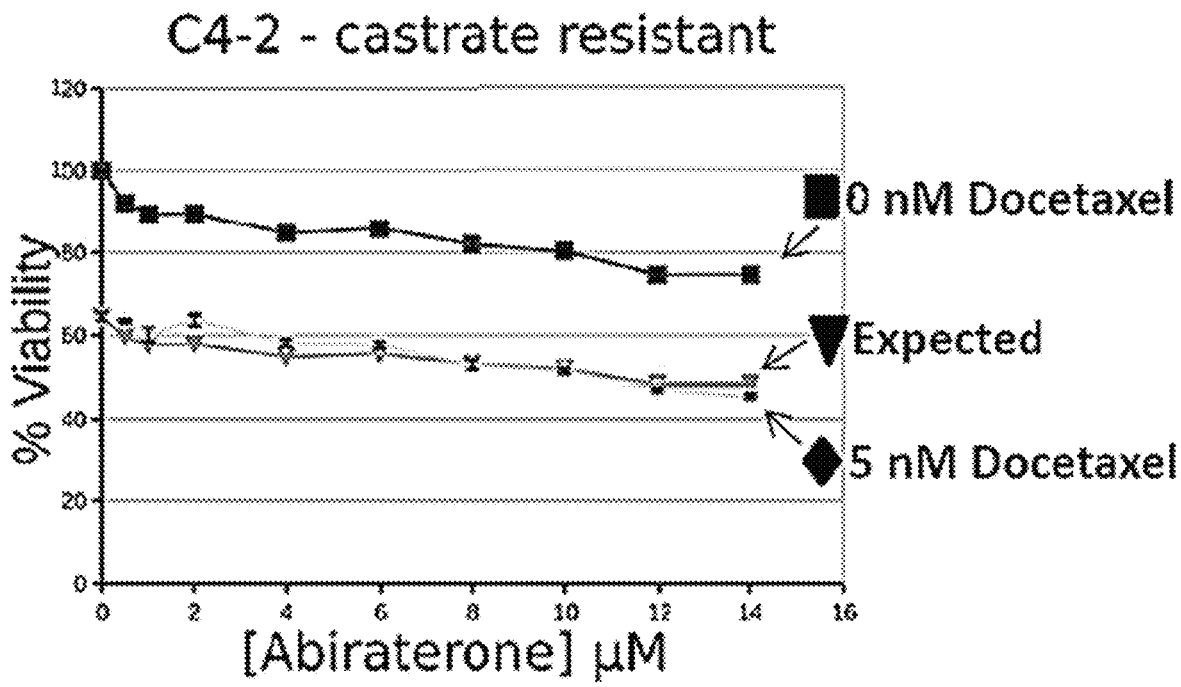
Figure 7C:
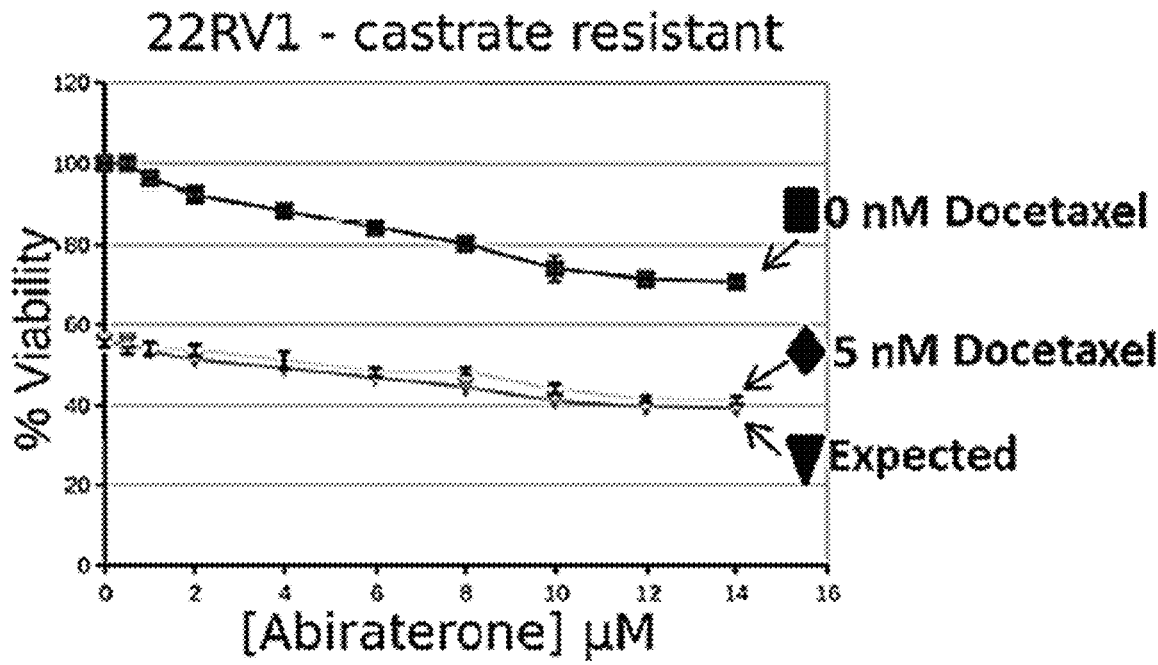

FIGS. 7A-7C show the results of assays measuring the % viability of cells (LNCaP-androgen dependent; 22 RV1-castrate resistant; and C4-2-castrate resistant) over time in presence of 5 nM docetaxel (-◆-) or absence (-■-) of 5 nM docetaxel and increasing concentrations of abiraterone. Docetaxel is a taxane, used in the treatment of CRPC, which prevents the depolymerization of microtubules resulting in mitotic arrest and subsequent death. This is thought to be the basis for its ability to target highly proliferative cancer cells. Expected results if the drugs were acting in an additive manner are also indicated (-▼-). Docetaxel, and the mitotic arrest caused by treatment with docetaxel, did not synergize with Abiraterone in prostate cancer cells, as judged by the overlapping observed and expected data.

This result can lead to a conclusion that it is not simply a G2/M arrest that leaves cells treated with BI2536 more sensitive to abiraterone. The results can also lead to a conclusion that the effect is not due to a loss of microtubule dynamics, which also occurs during loss of Plk1 kinase activity.

Example 5: Plk1 is Not a Generic Upstream Activator of the AR

Methods

Experiments were designed to investigate the molecular mechanism for the effects of combination Abiraterone/Plk1 inhibitor Treatment. C4-2 CRPC cells were grown in FBS and subjected to Abiraterone alone, or BI2536 alone, or the combination of Abiraterone and BI2536 for 24 hours. RNA was isolated for analysis by qPCR.

Results

Figure 8:
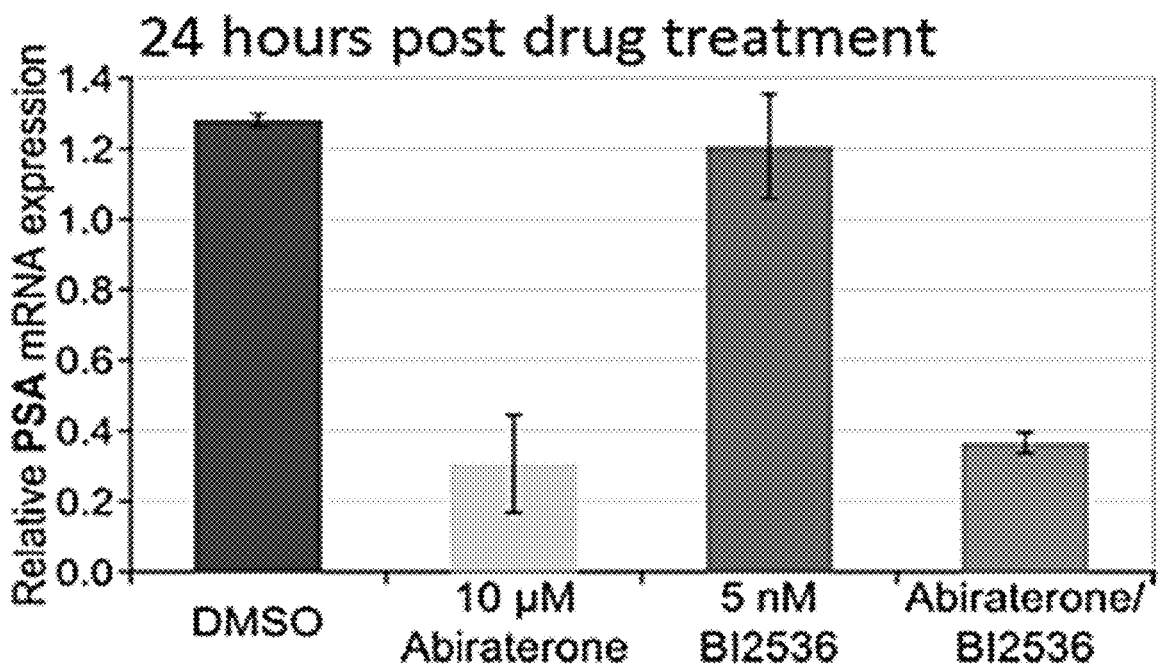
FIG. 8 is a bar graph showing the relative PSA mRNA expression of prostate cancer cells 24 hours post-treatment with DMSO; 10 µM abiraterone; 5 nM Plk inhibitor BI2536; and 10 µM abiraterone/5 nM Plk inhibitor BI2536, respectively.

Abiraterone substantially decreased the amount of PSA expression, however, the Plk1 inhibitor BI2536 did not suppress PSA expression alone and the combination of Abiraterone and BI2536 did not reduce PSA expression to any greater extent than Abiraterone alone (see FIG. 8).

These data indicated that Plk1 is not a generic activator of AR-driven gene expression, since the presence or absence of a potent Plk1 inhibitor has no effect on AR-driven PSA gene expression.

Instead, the data suggested there must be some other mechanism for the greater than additive effect of Plk1 inhibitor/Abiraterone than simply altering the AR transcriptional activity in a global manner. Thus, although Plk1 is not a generic regulator of the AR, perhaps Plk1 instead cooperates with the AR to regulate a subset of AR-dependent genes.

Example 6: Molecular Mechanism for Combination Abiraterone/Plk1 Inhibitor Treatment Involves Transcription Factors Elk1 and Nrf1/2

Methods

The molecular bases for combination Abiraterone/Plk1 inhibitor Treatment were examined using RNA-Seq experiments.

Since Plk1 inhibition results in mitotic arrest, but other clinically used drugs that cause mitotic arrest, such as taxanes, do not synergize with Abiraterone for tumor killing, the design of RNA-Seq-based gene expression experiments was carefully tailored to avoid being mis-lead by gene expression changes from the mitotic arrest phenotype. To eliminate the convoluted effects mitotic arrest exerts on transcription, which are not solely causative, doses of Plk1 inhibitor and Taxanes that resulted in comparable mitotic arrest were determined experimentally under six conditions (DMSO, 10 µM Abiraterone, BI2536 (Plk1 inhibitor), Abiraterone+BI2536, Docetaxol (a mitotic arrest control), and Abiraterone+ Docetaxol (as a mitotically-arrested non synergistic control with Abiraterone), see FIG. 9A).

Figures 9A, 9B:
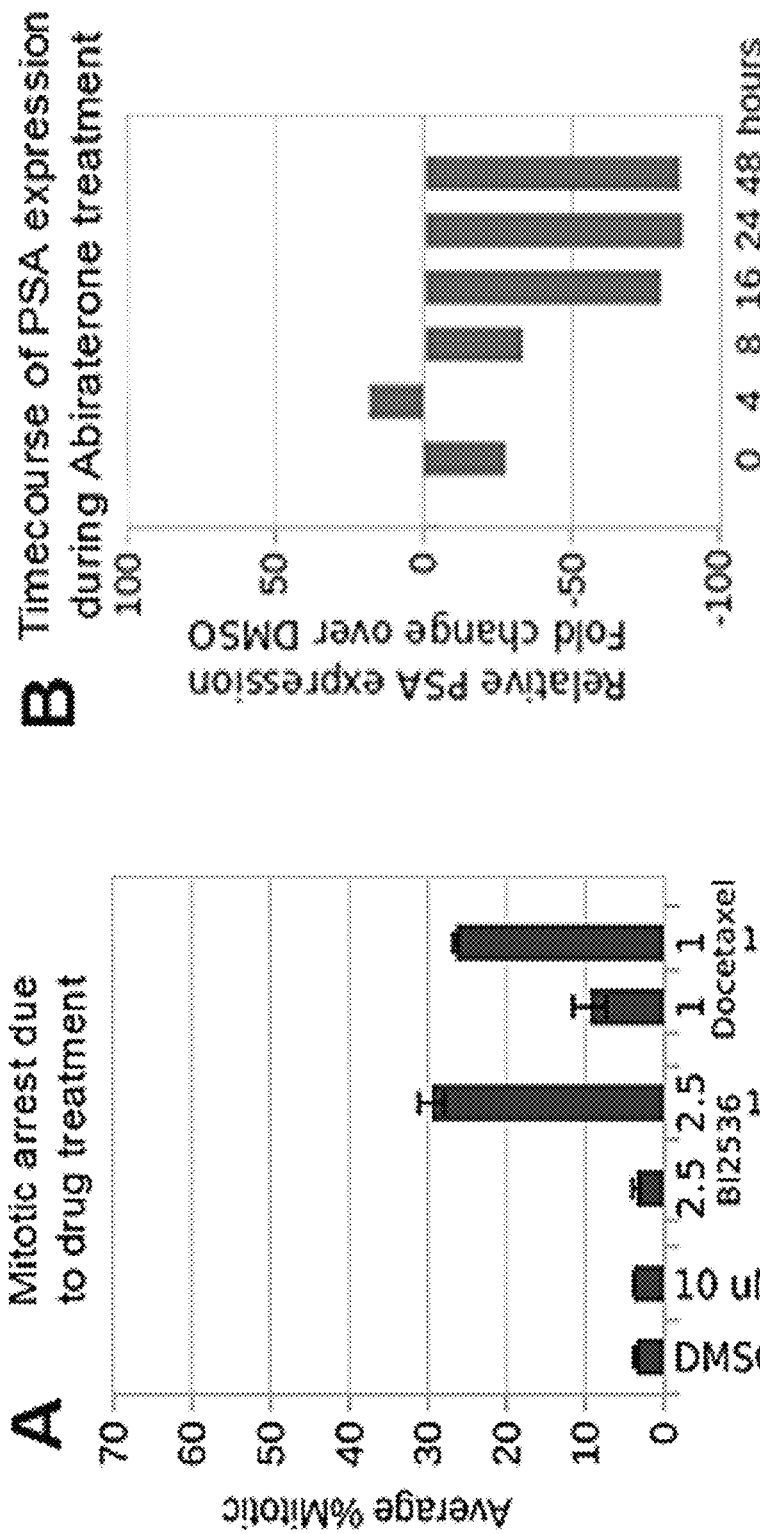
FIGS. 9A and 9B are bar graphs.
Figure 10A:
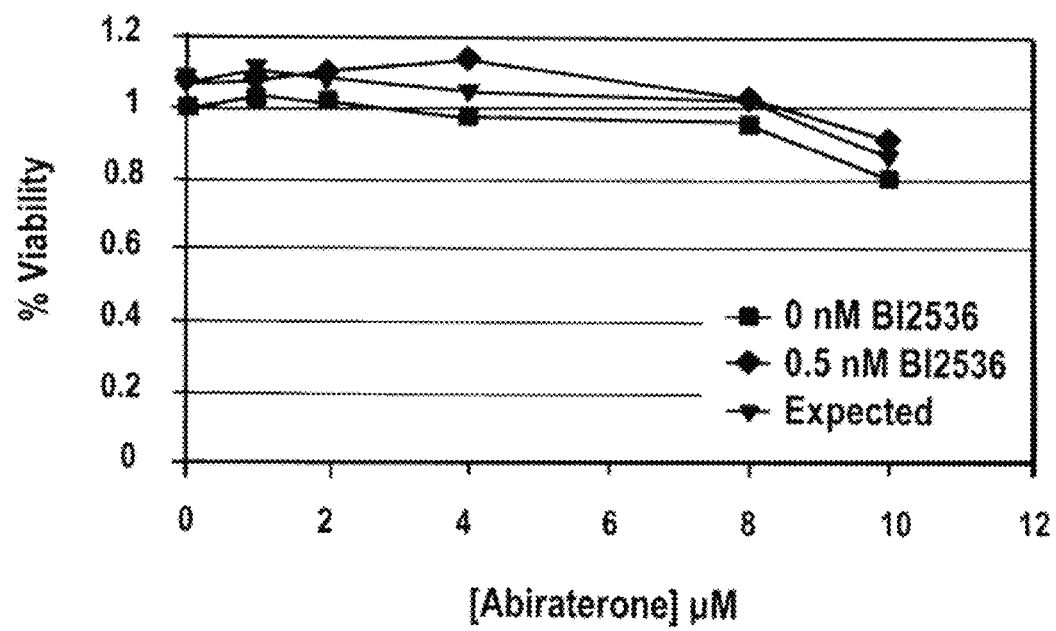
FIGS. 10A-10I; are line graphs demonstrating the % viability of SKBR3 cells in the presence of increasing concentrations of abiraterone (µM), and in the presence of Plk inhibitor 812536 at a range of concentrations (0.5 nm (FIG. 10A); 1 nm (FIG. 10B); 2 nm (FIG. 10C); 3 nm (FIG. 10D); 4 nm (FIG. 10E); 5 nm (FIG. 10F); 7.5 nm (FIG. 10G); 10 nm (FIG. 10H); and 10 nm (FIG. 10I), respectively (-◆-)); or absence (0 nm (-■-)) of Plk inhibitor BI2536. The predicted additive result of the two agents in combination is shown as "expected" (-▼-).
Figure 10B:
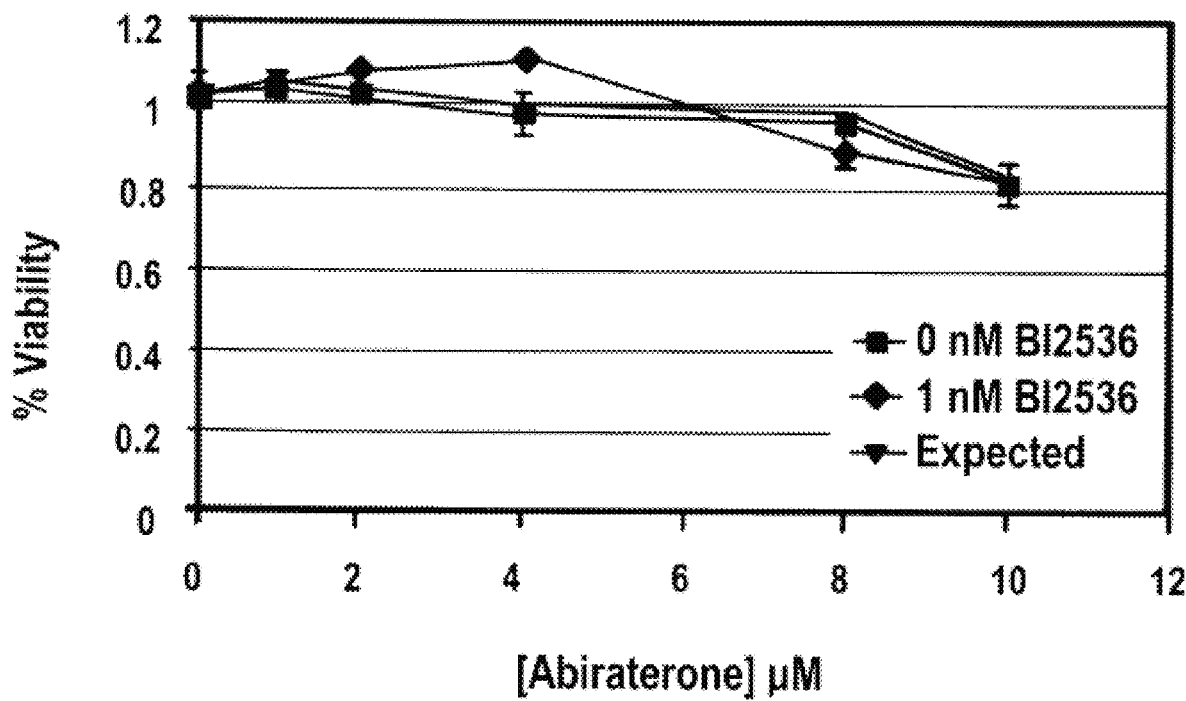
Figure 10C:
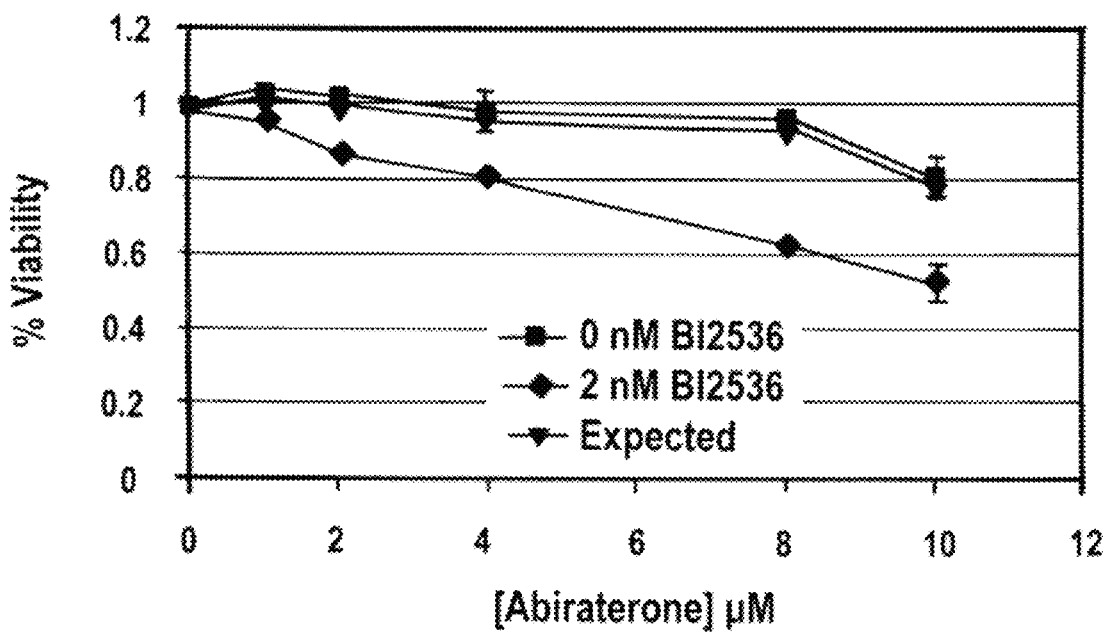
Figure 10D:
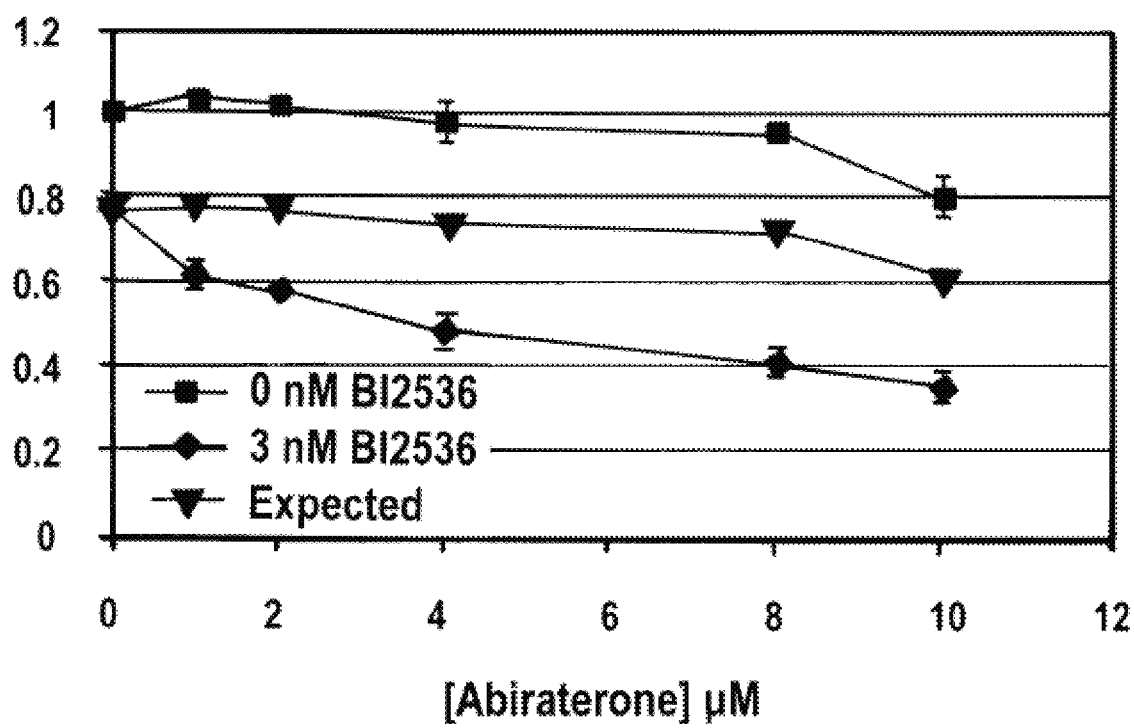
Figure 10E:
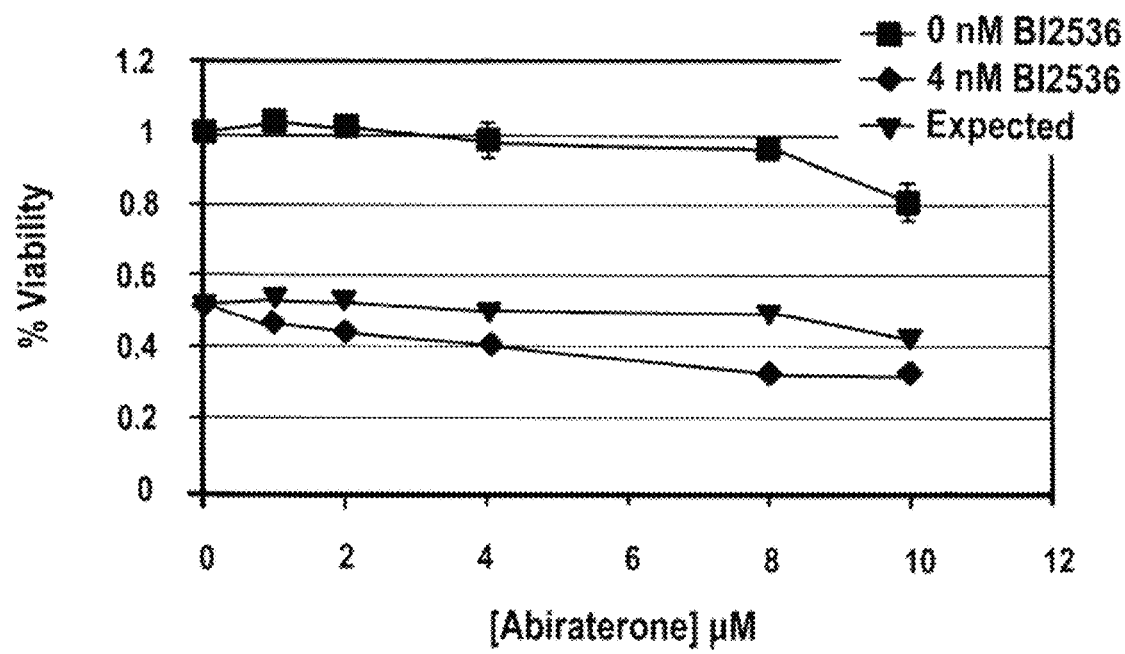
Figure 10F:
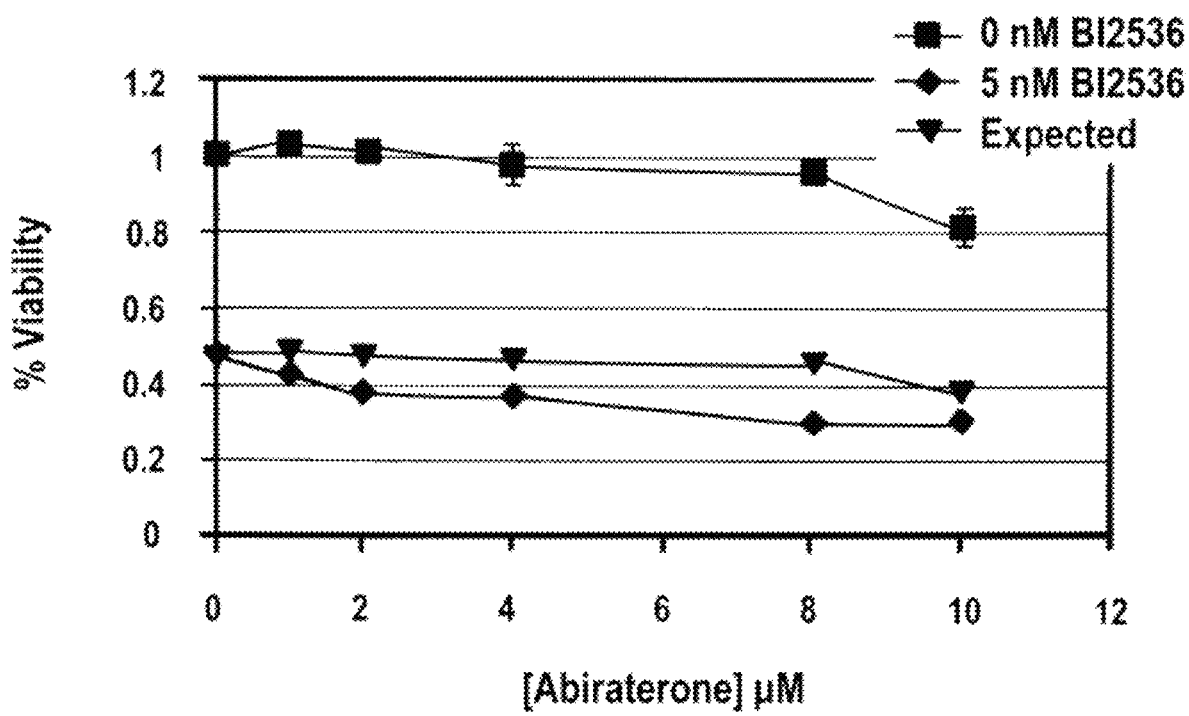
Figure 10G:
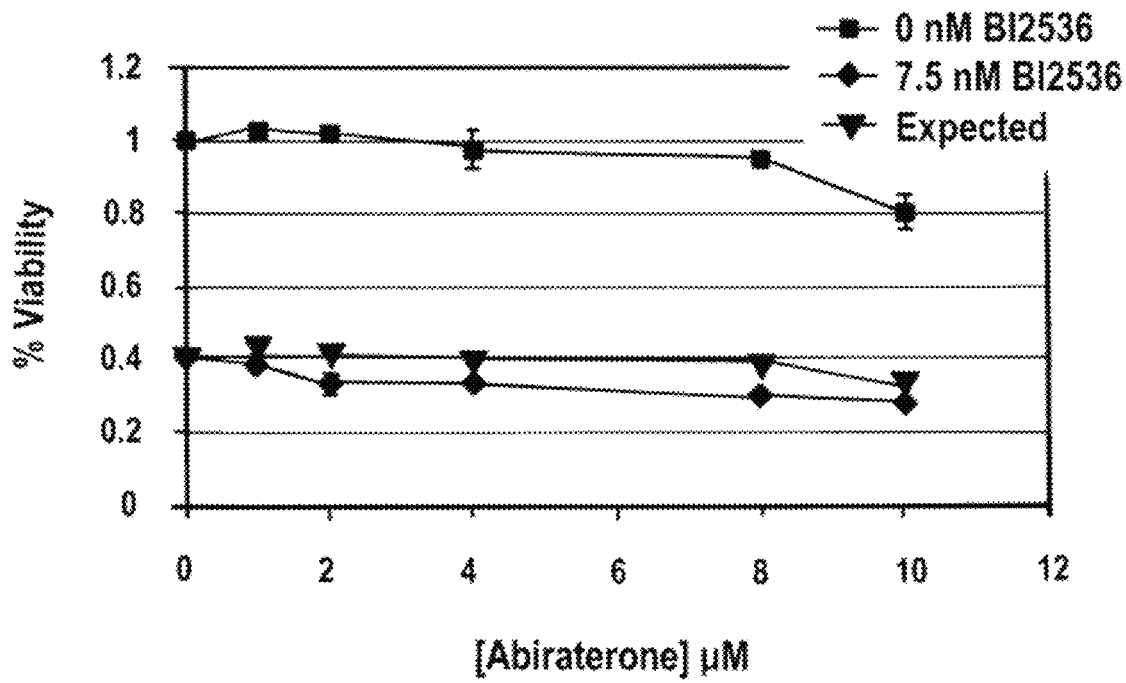
Figure 10H:
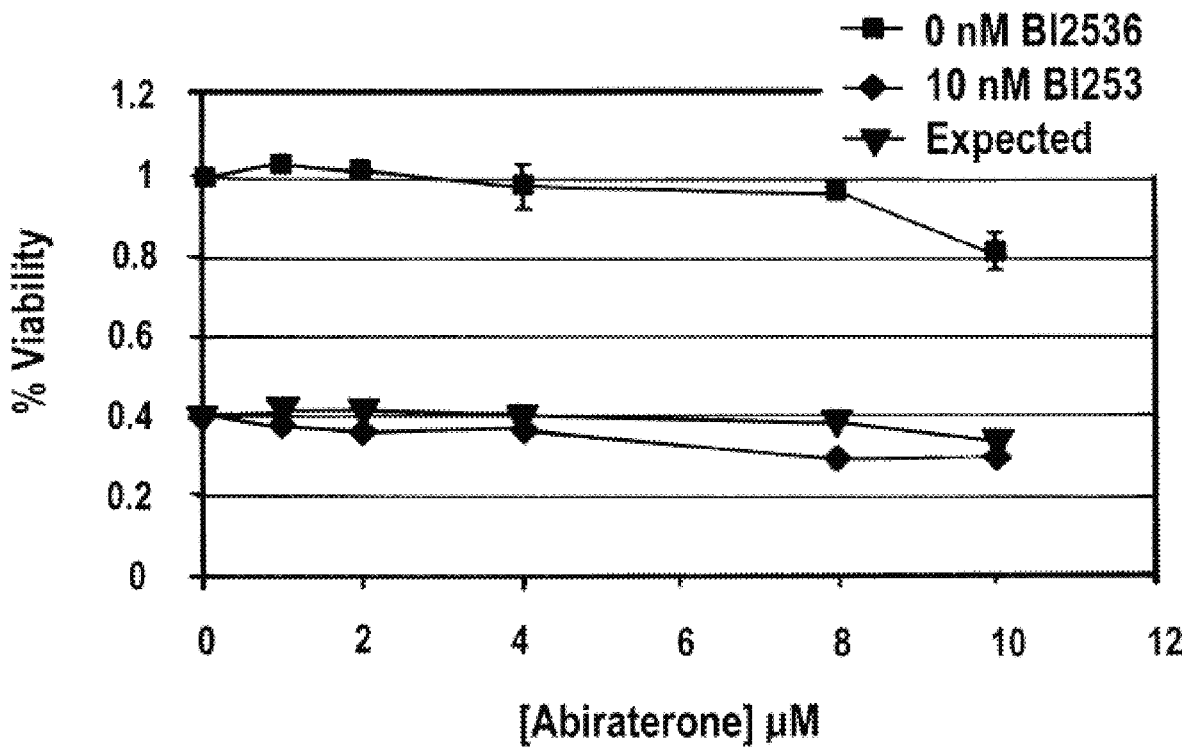
Figure 10I:
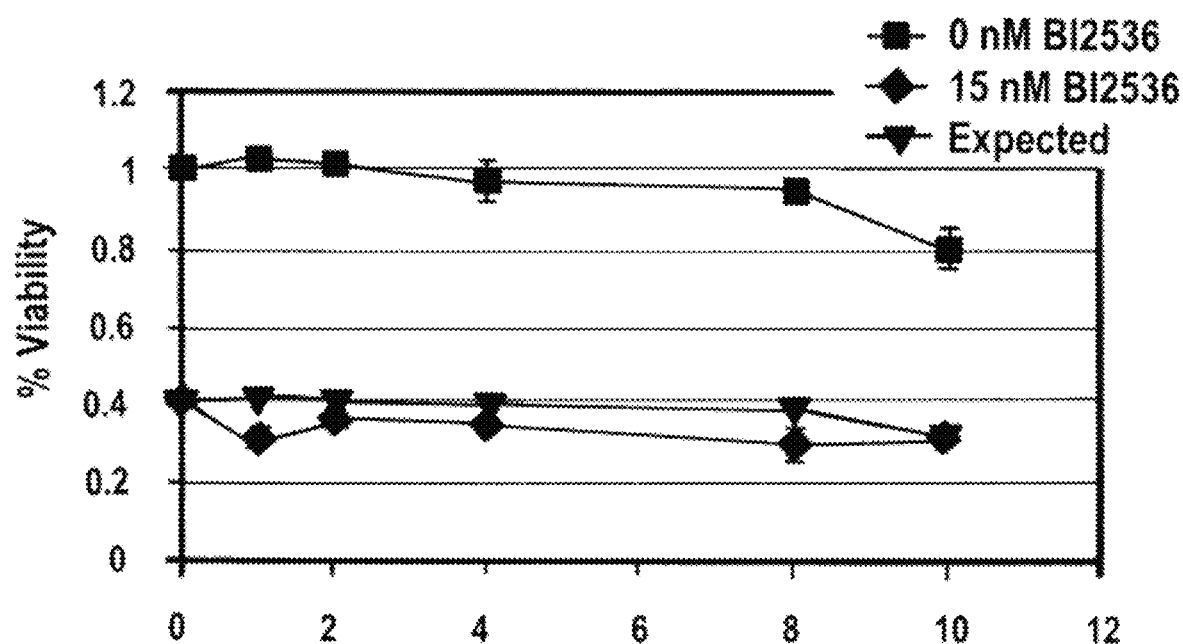

The strongly AR-dependent gene, PSA, was used as a means to determine the optimal time point for RNA isolation post drug treatment. Based on these analyses using changes in PSA expression as a function of time, 16 hours after treatment was selected as the earliest time point where Abiraterone-induced suppression of AR-driven gene expression could be detected (FIG. 9B).

RNA-Seq analysis of C4-2 cells was carried out to identify gene whose expression is changed specifically in cells treated with both Abiraterone and a Plk1 inhibitor. C4-2 cells were grown in media containing PBS and treated with the indicated drugs: 10 µM Abiraterone (Abi), 2.5 nM BI2536 (BI) and/or 1 nM Docetaxel (DTX) for 16 hours in triplicate prior to RNA-isolation. Reads (400 million) were aligned to the human genome and gene level expression data generated. The data was then transformed into robust z-scores. Differentially expressed genes (DEGs) of interest were identified using the statistical analysis of microarrays (SAM) package based on the following criteria: Significant difference between Abi vrs Abi BI; no significant difference between Abi vrs Abi DTX; and no significant difference between DMSO and Abi.

Computational analysis was performed for both up-regulated and down-regulated gene sets using both the DAVID (Database for Annotation, Visualization and Integrated Discovery) and GSEA (Gene Set Enrichment Analysis) algorithms to identify potential transcription factors whose activities were uniquely modulated by the combined Plk1 inhibition/Abiraterone treatment.

Results

The experiments identified Genes whose expression changed (induced or repressed) at the 16 hour time point specifically in response to by the combination of Abiraterone and Plk1 inhibition by BI2536, but not in response to Abiraterone alone.

The data identified multiple genes of interest. Within this list of genes there is a highly significant enrichment of genes which have been found to contain binding sites for the transcription factors Elk1 and Nrf1/2 adjacent to their transcriptional start site. Thus, the combined analyses implicated both Elk1 and Nrf1/2 as critical targets for Plk1i/Abiraterone effects. Nrf1/2 is a particularly interesting potential mechanistic target that rationalizes the greater than additive combinatorial effect.

Example 7: A Significant Subset of Breast Cancer Cell Lines Display Synergistic Killing by Combination Abiraterone Plus Plk1 Inhibition Methods Experiments were conducted to quantify the greater than additive effect between Abiraterone and Plk1 inhibitors.

A very comprehensive series of experiments was performed in 23 cell lines using combinations of 9 different doses of the Plk1 inhibitor and 6 different doses of Abiraterone. Cell lines were subjected to a dose response matrix of increasing concentrations of Abiraterone (0 to 10 µM) and BI2536 (0 to 15 nM) and assessed for viability after 3 days using Cell Titer Glo™. Greater than additive killing by the combination of Plk1 inhibitors plus abiraterone was measured after 3 days and quantified by summing the difference between the areas under the curve (AUC) for expected killing assuming only drug additivity (▼; FIGS. 10A-10I) and the measured cell killing (◆; FIG. 10A-10I), for increasing concentrations of Abiraterone for each dose of BI2536 (Total dAUC) (see FIGS. 10A-10I).

These numbers were then correlated with mRNA expression datasets obtained from the Cancer Cell Line Encyclopedia (CCLE) and the entire matrix was transformed into robust scores.

Results

These experiments revealed that a substantial subset of the breast cancer cell lines tested showed greater than additive killing. The data also provided information on the sensitivity of each cell line to abiraterone alone. Further more than additive effects for some cell lines is apparent only after 5 days of treatment.

Figure 11:
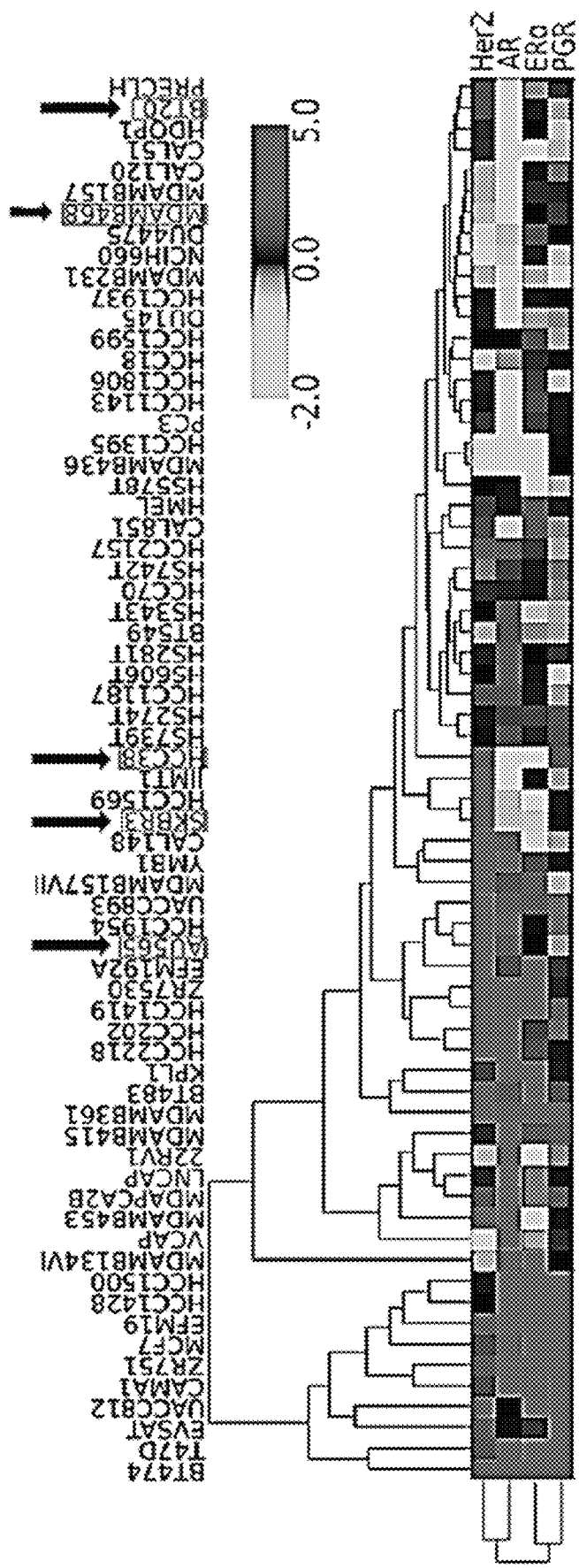
FIG. 11 is a schematic heat map showing different breast cancer cell lines (at top) in relation to expression of Her2; Androgen Receptor (AR; indicated by arrow at right of schematic); estrogen receptor alpha (ERα); and Progesterone Receptor (PGR). Breast cancer cell lines that displayed more than additive efficacy of Abiraterone and Plk1 inhibition are indicted by bold arrows.

The relative expression of the estrogen receptor alpha (ERα), the AR, the progesterone receptor (PGR) and Her2 were plotted according to the Cancer Cell Line Encyclopedia (CCLE) (FIG. 11). The relative position of genes on the plot demonstrated that a significant portion of breast cancer cell lines express the androgen receptor. However, the breast cancer cell lines that displayed greater than additive effect of Abiraterone and Plk1 inhibition (indicted by full arrows in FIG. 11) do not appear to depend on AR signaling or show any other consistent expression of these steroid hormone or growth factor genes. In fact, the majority of the synergistic cell lines are derived from triple-negative breast tumors (TNBCs), and the sensitivity of the cells to combination treatment does not appear to correlate with androgen receptor expression, or with estrogen receptor expression (FIG. 11). Furthermore, profound greater than additive effect was also observed in some non-hormonal tumor types including pancreatic cancer. This has potentially important clinical implications since effective chemotherapy for TNBCs, and pancreatic cancer remains a high-priority unmet need. These data clearly indicated that Abiraterone, in combination with Plk1 inhibition, can have utility far beyond prostate cancer.

Example 8: Tumor Cell Lines that are Sensitive to Combined Abiraterone/Plk1 Inhibition Treatment have a Gene Expression Signature Methods Experiments were conducted to determine the molecular signature of up- and down-regulated genes whose expression correlates very well with sensitivity to combined Abiraterone/Plk1 inhibition treatment. To understand why certain cancer cell lines showed marked greater than additive effects to combination Abiraterone/Plk1 inhibition treatment, cell lines were ranked by "synergy score" (i.e., observed additive effect of combination Abiraterone/Plk1 inhibition treatment), and cross-correlated with gene expression data.

Comprehensive gene expression values for each of the cell lines were obtained from the Cancer Cell Line Encyclopedia (CCLE), and used for clustering analysis based on synergy score ranking. Correlation between the synergy score ranking and expression of any given gene was calculated by Pearson correlation coefficients and the genes were then plotted on a graph and ranked in order from most to least correlated with the observed amount of synergy score. These data were then used to determine which genes were associated with synergy.

Results

Gene set enrichment analysis performed on the sensitivity-ranked cell lines indicated that synergistic cell lines showed a less mesenchymal pattern of gene expression, up-regulation of cholesterol biosynthesis, and decreased expression of mitochondrial/oxidative phosphorylation genes.

Importantly, within the top 30 genes whose up-regulation correlated with strong synergy score to combination treatment are 4 components of the Retinoic Acid Receptor (RA) signaling pathway. Cell lines which displayed the most greater than additive effect had high expression levels of several genes involved in retinoic acid signaling, including Retinoic Acid Receptor Alpha (RARA); Retinoic Acid Receptor Gamma (RARG); Retinol Dehydrogenase (ADH4); and Retinaldehyde Reductase (DHRS3). Of these four genes, RARA was the gene most highly correlated with synergy score, with a Pearson correlation coefficient of 0.806, p=0.000031.

The RA signaling pathway is a nuclear hormone signaling pathway similar to, but distinct from the AR and ER pathways, that has pleiotropic roles in cell growth and differentiation. Abnormalities in RA receptor signaling have been clearly implicated in breast and hematological malignancies. The pathway appears to have differential effects in normal versus cancer cells, and in certain cancer types, RA signaling appears to be important for proliferation and resistance to apoptosis (Noy, *Annu Rev Nutr*, pp. 201-217 (2010)). It has been shown that retinoic acid signaling markedly potentiated the ability of Plk1 inhibitors to kill cells. (Liu-Sullivan, et al., *Oncotarget*, pp. 1254-1264 (2011)). Furthermore, there is clear data that RA signaling suppresses Nrf1/2-driven gene expression, and that signaling through the androgen receptor suppresses the RA signaling that regulates Nrf½-driven genes (Schultz, et al., *PLoS ONE*, pp. e87204 (2014); Wang, et al., *PNAS USA*, pp. 19589-19594 (2007)).

Thus, these data strongly suggest a model for Abiraterone action in which Abiraterone inhibition of androgen signaling results in up-regulation of RA signaling due to nuclear hormone pathway cross-talk. The RA up-regulation makes the cells sensitive to Plk1 inhibition.

In addition, the combined effects of Plk1 inhibition and RA up-regulation specifically modualtes Nrf1/2-driven genes, many of which are involved in mitochondria) oxidative phosphorylation and anti-oxidant responses, thereby explaining the gene expression data for combination treatments, as well as the sensitivity of specific tumor cell types. This model can provide a means to select tumors for combinatorial treatment, provide a direct measurement of treatment response that could be followed clinically, rationalize the mechanism for Abiraterone resistance, and provide a new series of drug targets (the RA pathway) that could be used to enhance Abiraterone's effectiveness as an anti tumor agent.

Example 9: The p38MAPK-MK Pathway Influences the Response of Tumors to Abiraterone Methods Experiments were conducted to investigate the role of the p38MAPK-MK2 pathway in prostate cancer, Western blotting was used to investigate up-regulation of MK3 and MK5 protein levels in LNCaP cells after MK2 knock down using shRNA. No change was observed in 22Rv1 or C4-2 cells. RiLNCaP cell viability was measured using Cell-Titer Glo in response to 10, 20 or 40 µM of the p38MAPK inhibitor SB203580 in the presence or absence of 10 µM Abiraterone (FIG. 12).

Experiments were also conducted to determine the effects of p38 inhibition on Abiraterone sensitivity in Prostate Cancer cell lines. Cell viability of PCa cell lines to increasing doses (10, 20 and 40 µM) of the p38MAPK inhibitor SB203580, as measured using Cell Titer Glo (FIG. 13A). The effect of increasing doses of SB203580 (µM) on the extent of PCa cell killing by 10 µM Abiraterone was also assessed (FIG. 13B). The effects of the two drugs appear to be additive.

Results

The data indicated that MK2 inhibition, which partially suppresses hsp27phosphorylation, had little effect on survival of prostate cancer cell lines. These results were unusual, since there is a reasonably solid body of evidence indicating that phospho-hsp27 is required for nuclear chaperoning of the activated form of the androgen receptor. The lack of effect of MK2 disruption on PCa survival was attributed to possible up-regulation of MK3 and/or MK5 kinases, both of which might partially subsume the role of MK2 in hsp27 phosphorylation.

Up-regulation of both MK3 and MK5 was observed in LNCaP cells but not in 22Rv1 or C4-2 cells. Importantly, inhibition of the upstream kinase, p38MAPK, by small molecule inhibitors resulted in cell death in the MK2 knockdown LNCaP cells, in agreement with the hypothesis that the pathway was re-wired.

Furthermore, p38MAPK inhibition alone was able to cause small amounts of cell death in all of the cell lines, but more marked levels of death were only observed at rather high levels of the p38 inhibitor (FIG. 13A). The p38MAPK inhibitor also modestly enhanced the ability of Abiraterone to kill all of the PCa cell lines (FIG. 13B).

Further experiments were conducted to include co-culture using endothelial cells. These data indicated that conditioned media from HUVEC cells partially protected the PCa cells from Abiraterone or taxane-induced cell death. The data further indicated that MK2 signaling in the endothelial cells is necessary for the Abiraterone and taxane-resistance.

Thus, the p38MAPK-MK2 pathway appears to play complex roles in integrating the tumor response to Abiraterone through effects in both the tumor cells and the tumor microenvironment. In addition, there is evidence that the p38MAPK/MK2 pathway can also influences the RA signaling pathway (Gianni, et al., The EMBO journal 25, 739-751 (2002); Gianni, et al., The EMBO journal 21, 3760-3769 (2002)).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating cancer, comprising administering NMS-1286937 (Onvansertib) and an antiandrogen or androgen antagonist to a subject, wherein the cancer is a solid tumor cancer.

2. The method of claim 1, wherein the solid tumor cancer is an advanced or metastatic solid tumor cancer.

3. The method of claim 1, wherein the solid tumor cancer is prostate cancer, breast cancer, ovarian cancer, or endometrial cancer.

4. The method of claim 1, wherein the solid tumor cancer is metastatic castration- resistant prostate cancer.

5. The method of claim 1, wherein the antiandrogen or androgen antagonist is abiraterone.

6. The method of claim 5, further comprising administering to the subject a steroid.

7. The method of claim 5, wherein the steroid is administered to the subject through the same route of administration as NMS-1286937 (Onvansertib) and/or the antiandrogen or androgen antagonist.

8. The method of claim 5, wherein the steroid is prednisone or prednisolone.

9. The method of claim 5, wherein abiraterone and the steroid are administered to the subject daily or twice daily.

10. The method of claim 1, wherein NMS-1286937 (Onvansertib) and the antiandrogen or androgen antagonist are administered to the subject through the same route of administration.

11. The method of claim 10, wherein NMS-1286937 (Onvansertib) and/or the antiandrogen or androgen antagonist is administered to the subject orally.

12. The method of claim 11, wherein NMS-1286937 (Onvansertib) and/or the antiandrogen or androgen antagonist is administered to the subject in an oral dosage form selected from the group consisting of tablets, capsules, solutions, suspensions, syrups, and lozenges.

13. The method of claim 1, wherein NMS-1286937 (Onvansertib) and the antiandrogen or androgen antagonist are administered simultaneously.

14. The method of claim 1, wherein the antiandrogen or androgen antagonist is administered to the subject prior to the administration of NMS-1286937 (Onvansertib).

15. The method of claim 1, wherein the administration of the antiandrogen or androgen antagonist and the administration of NMS-1286937 (Onvansertib) partially overlap.

16. The method of claim 15, wherein the subject is administered with NMS-1286937 (Onvansertib) and/or the antiandrogen or androgen antagonist for 5, 15 or 25 days or one, two or three weeks.

17. The method of claim 1, wherein the subject is administered with NMS-1286937 (Onvansertib) and/or the antiandrogen or androgen antagonist for up to 25 days.

18. The method of claim 1, wherein the subject is administered with NMS-1286937 (Onvansertib) in a dosage from about 0.0001 mg/kg of body weight to about 100 mg/kg of body weight per day.

19. The method of claim 1, wherein the subject is administered with abiraterone in an amount of 10-2,000 mg/patient per day.

20. The method of claim 1, wherein the antiandrogen or androgen antagonist is administered to the subject 1, 2, 3, 5, 10, 15, 20, 24 or 30 hours or days prior to the administration of NMS-1286937 (Onvansertib).

* * * * *